(12) United States Patent
Borgmeier et al.

(10) Patent No.: US 7,019,169 B2
(45) Date of Patent: Mar. 28, 2006

(54) PREPARATION OF (METH)ACRYLIC ACID

(75) Inventors: Frieder Borgmeier, Mannheim (DE);
Frank Rosowski, Mannheim (DE);
Hans-Günther Lintz, Karlsruhe (DE);
Ina Grisstede, Karlsruhe (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/934,442

(22) Filed: Sep. 7, 2004

(65) Prior Publication Data

US 2005/0065370 A1 Mar. 24, 2005

Related U.S. Application Data

(60) Provisional application No. 60/504,957, filed on Sep. 23, 2003.

(30) Foreign Application Priority Data

Sep. 23, 2003 (DE) ................. 103 44 264

(51) Int. Cl.
*C07C 51/16* (2006.01)
(52) U.S. Cl. ................................ 562/549
(58) Field of Classification Search .......... None
See application file for complete search history.

(56) References Cited

U.S. PATENT DOCUMENTS

| | | | |
|---|---|---|---|
| 4,297,247 A | 10/1981 | Krabetz et al. | |
| 4,438,217 A | 3/1984 | Takata et al. | |
| 4,537,874 A | 8/1985 | Sato et al. | |
| 4,656,157 A | 4/1987 | Hofmann et al. | |
| 5,364,825 A | 11/1994 | Neumann et al. | |
| 5,449,821 A | 9/1995 | Neumann et al. | |
| 5,583,086 A | 12/1996 | Tenten et al. | |
| 5,677,261 A | 10/1997 | Tenten et al. | |
| 5,739,391 A | 4/1998 | Ruppel et al. | |
| 5,821,390 A | 10/1998 | Ruppel et al. | |
| 5,910,608 A | 6/1999 | Tenten et al. | |
| 6,036,880 A | 3/2000 | Komada et al. | |
| 6,063,728 A | 5/2000 | Hinago et al. | |
| 6,143,916 A | 11/2000 | Hinago et al. | |
| 6,169,214 B1 | 1/2001 | Tenten et al. | |
| 6,294,685 B1 | 9/2001 | Ushikubo et al. | |
| 6,383,976 B1 | 5/2002 | Arnold et al. | |
| 6,395,936 B1 | 5/2002 | Arnold et al. | |
| 6,525,217 B1 | 2/2003 | Unverricht et al. | |
| 6,610,629 B1 | 8/2003 | Hinago et al. | |
| 2003/0017944 A1 | 1/2003 | Hinago et al. | |
| 2003/0088124 A1 | 5/2003 | Dubois | |
| 2004/0034249 A1 | 2/2004 | Arnold et al. | |
| 2004/0054222 A1 | 3/2004 | Felder et al. | |
| 2004/0062870 A1 | 4/2004 | Dieterle et al. | |
| 2004/0063988 A1 | 4/2004 | Hechler et al. | |
| 2004/0082810 A1 | 4/2004 | Borgmeier et al. | |
| 2004/0097368 A1 | 5/2004 | Borgmeier et al. | |
| 2004/0102648 A1 | 5/2004 | Borgmeier et al. | |
| 2004/0138500 A1 | 7/2004 | Borgmeier | |
| 2004/0192965 A1 | 9/2004 | Petzoldt et al. | |
| 2004/0204607 A1 | 10/2004 | Machhammer et al. | |

FOREIGN PATENT DOCUMENTS

| | | |
|---|---|---|
| DE | 29 09 671 | 10/1980 |
| DE | 33 00 044 | 7/1983 |
| DE | 33 38 380 | 4/1984 |
| DE | 44 07 020 | 9/1994 |
| DE | 44 31 957 | 3/1995 |
| DE | 44 42 346 | 5/1996 |
| DE | 198 35 247 | 2/1999 |
| DE | 198 55 913 | 6/2000 |
| DE | 199 10 506 | 9/2000 |
| DE | 199 48 523 | 4/2001 |
| DE | 100 29 338 | 1/2002 |
| DE | 100 46 672 | 3/2002 |
| DE | 100 46 957 | 4/2002 |
| DE | 100 51 419 | 4/2002 |
| DE | 101 21 592 | 5/2002 |
| DE | 101 22 027 | 5/2002 |
| DE | 101 45 958 | 5/2002 |
| DE | 101 01 695 | 7/2002 |
| DE | 101 18 814 | 10/2002 |
| DE | 102 54 278 | 2/2004 |
| DE | 102 46 119 | 4/2004 |
| DE | 102 61 186 | 7/2004 |
| DE | 103 13 208 | 10/2004 |
| DE | 103 13 213 | 10/2004 |
| DE | 103 16 465 | 10/2004 |
| DE | 103 25 487 | 12/2004 |

(Continued)

OTHER PUBLICATIONS

Derwent Publications, JP 2000-256257, Sep. 19, 2000.

(Continued)

*Primary Examiner*—Paul A. Zucker
(74) *Attorney, Agent, or Firm*—Oblon, Spivak, McClelland, Maier & Neustadt, P.C.

(57) ABSTRACT

A process for preparing (meth)acrylic acid by conducting a saturated hydrocarbon precursor compound through a catalyst bed I whose catalysts I have, as the active composition, a multimetal oxide I which has a specific X-ray diffractogram and contains the elements Mo and V, at least one of the elements Te and Sb, and also at least one of the elements from the group consisting of Nb, Ta, W, Ce and Ti, wherein the catalyst bed I is interrupted by at least one catalyst bed II whose catalysts II have, as the active composition, a multimetal oxide II which contains the elements Mo, Bi and Fe.

18 Claims, 3 Drawing Sheets

FOREIGN PATENT DOCUMENTS

| | | |
|---|---|---|
| DE | 103 38 529 | 4/2005 |
| EP | 0 000 835 | 2/1979 |
| EP | 0 184 790 | 6/1986 |
| EP | 0 279 374 | 8/1988 |
| EP | 0 293 859 | 12/1988 |
| EP | 0 529 853 | 3/1993 |
| EP | 0 575 897 | 12/1993 |
| EP | 0 603 836 | 6/1994 |
| EP | 0 608 838 | 8/1994 |
| EP | 0 700 893 | 3/1996 |
| EP | 0 714 700 | 6/1996 |
| EP | 0 895 809 | 2/1999 |
| EP | 0 962 253 | 12/1999 |
| EP | 1 080 784 | 3/2001 |
| EP | 1 090 684 | 4/2001 |
| EP | 1 106 598 | 6/2001 |
| EP | 1 123 738 | 8/2001 |
| EP | 1 192 982 | 4/2002 |
| EP | 1 192 983 | 4/2002 |
| EP | 1 192 986 | 4/2002 |
| EP | 1 192 987 | 4/2002 |
| EP | 1 192 988 | 4/2002 |
| EP | 1 193 240 | 4/2002 |
| EP | 1 238 960 | 9/2002 |
| EP | 1 254 706 | 11/2002 |
| EP | 1 254 707 | 11/2002 |
| EP | 1 254 709 | 11/2002 |
| WO | WO 99/03825 | 1/1999 |
| WO | WO 00/29106 | 5/2000 |
| WO | WO 02/24620 | 3/2002 |
| WO | WO 02/083615 | 10/2002 |
| WO | WO 03/039744 | 5/2003 |

OTHER PUBLICATIONS

Derwent Publications, JP 10-36311, Feb. 10, 1998.
Derwent Publications, JP 11-57479, Mar. 2, 1999.
E. Balcells, et al., "Partial oxidation of propane and propene to acrylic acid over a Mo-V-Te-Nb oxide catalyst", Catalysis Letters, vol. 87, No. 3-4, Apr. 2003, pp. 195-199.
Derwent Publications, JP 7-315842, Dec. 5, 1995.
Kenji Nomiya, et al., "Anderson-Type Heteropolyanions of Molybdenum (VI) and Tungsten(VI)", Polyhedron, vol. 6, No. 2, 1987, pp. 213-218.
W. Ueda, et al., "Selective Oxidation of $C_1$-$C_3$ Alkanes over Molybdenum-and Vanadium-based Oxide Catalysts", Kinetics and Catalysis, vol. 40, No. 3, 1999, pp. 401-404.
Derwent Publications, JP 2000-143244, May 23, 2000.

PREPARATION OF (METH)ACRYLIC ACID

BACKGROUND OF THE INVENTION

1. Field of the Invention

The present invention relates to a process for preparing (meth)acrylic acid by heterogeneously catalyzed gas phase partial oxidation of at least one saturated hydrocarbon precursor compound at elevated temperature, by conducting a starting reaction gas mixture comprising the at least one saturated hydrocarbon precursor compound, molecular oxygen and at least one inert gas through at least one catalyst bed I whose catalysts I are such that their active composition is at least one multimetal oxide I which contains the elements Mo and V, at least one of the elements Te and Sb, and at least one of the elements from the group consisting of Nb, Ta, W, Ce and Ti, and whose X-ray diffractogram is an X-ray diffractogram I which has reflections h, i and k whose peak locations are at the reflection angles (2Θ) of $22.2\pm0.5°$ (h), $27.3\pm0.5°$ (i) and $28.2\pm0.5°$ (k), the reflection h being the most intense within the X-ray diffractogram I and also having a half-height width of at most $0.5°$, and the half-height width of the reflection i and of the reflection k each being $\leq 1°$.

2. Description of the Related Art

In this document, the notation (meth)acrylic acid is an abbreviation for methacrylic acid or acrylic acid.

(Meth)acrylic acid forms reactive monomers which are suitable, for example, for preparing polymers which may find use as adhesives, among other uses.

On the industrial scale, one way of preparing (meth)acrylic acid is by heterogeneously catalyzed gas phase partial oxidation of propane or isobutane.

Acrylic acid and methacrylic acid can be obtained in a mixture by heterogeneously catalyzed gas phase partial oxidation of a mixture of propane and isobutane.

Propane and isobutane are therefore referred to in this document as saturated hydrocarbon precursor compounds of (meth)acrylic acid.

Processes for preparing (meth)acrylic acid by heterogeneously catalyzed gas phase partial oxidation of at least one saturated hydrocarbon precursor compound according to the preamble of this document are known (cf., for example, EP-A 1192987, DE-A 10122027, JP-A 2000-256257, EP-A 608838, EP-A 1193240, EP-A 1238960, EP-A 962253, JP-A 10-36311, EP-A 1254706, DE-A 10051419, WO-A 99/003825, JP-A 11-57479 and DE-A 10338529).

A disadvantage of these processes is that the selectivity of the (meth)acrylic acid target compound which becomes established at a given conversion of the saturated hydrocarbon precursor compound is not fully satisfactory.

It is an object of the present invention to provide an improved process with regard to the selectivity of the target compound for a given conversion of the saturated hydrocarbon precursor compound.

SUMMARY OF THE INVENTION

We have found that this object is achieved by a process for preparing (meth)acrylic acid by heterogeneously catalyzed gas phase partial oxidation of at least one saturated hydrocarbon precursor compound at elevated temperature, by conducting a starting reaction gas mixture comprising the at least one saturated hydrocarbon precursor compound, molecular oxygen and at least one inert gas through at least one catalyst bed I whose catalysts I are such that their active composition is at least one multimetal oxide I which contains the elements Mo and V, at least one of the elements Te and Sb, and at least one of the elements from the group consisting of Nb, Ta, W, Ce and Ti, and whose X-ray diffractogram is an X-ray diffractogram I which has reflections h, i and k whose peak locations are at the reflection angles (2Θ) of $22.2\pm0.5°$ (h), $27.3\pm0.5°$ (i) and $28.2\pm0.5°$ (k), the reflection h being the most intense within the X-ray diffractogram I and also having a half-height width of at most $0.5°$, and the half-height width of the reflection i and of the reflection k each being $\leq 1°$, wherein the gas phase partial oxidation of the reaction gas mixture over the catalysts I in the at least one catalyst bed I is interrupted at least once by continuing the gas phase partial oxidation in at least one catalyst bed II whose catalysts II are such that their active composition is at least one multimetal oxide II whose X-ray diffractogram is different to the X-ray diffractogram I and has a stoichiometry of the general formula A, $$Mo_{12}Bi_aFe_bX^1_cX^2_dX^3_eX^4_fO_n \quad (A)$$

where
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.2 to 5,
b=from 0.01 to 5,
c=from 0 to 10,
d=from 0 to 2,
e=from 0 to 8,
f=from 0 to 10 and
n=a number which is determined by the valency and frequency of the elements in A other than oxygen, or a stoichiometry of the general formula B $$[Y^1_{a'}Y^2_{b'}O_{x'}]_p[Y^3_{c'}Y^4_{d'}Y^5_{e'}Y^6_{f'}Y^7_{g'}Y^2_{h'}O_{y'}]_q \quad (B)$$

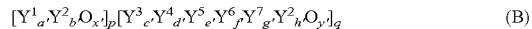

where
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements vanadium, chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from >0 to 20,
f'=from 0 to 6,
g'=from 0 to 15,
h'=from 8 to 16,
x', y'=numbers which are determined by the valency and frequency of the elements in B other than oxygen and
p, q=numbers whose p/q ratio is from 0.1 to 10.

Figure 1:
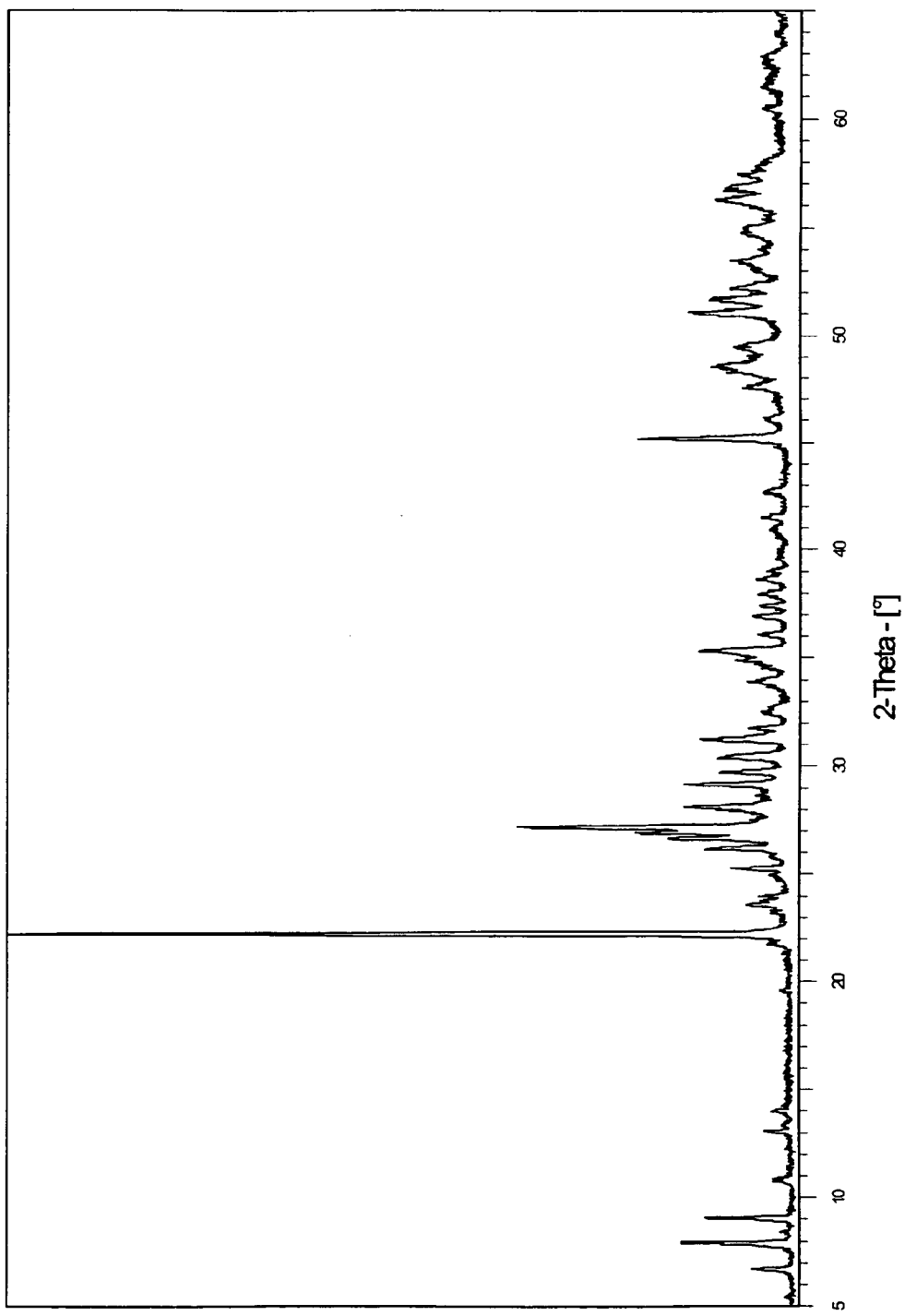
FIG. 1 shows the X-ray diffractogram of a pure i phase composition of $Mo_{1.0}V_{0.29}Te_{0.14}Nb_{0.13}O_x$.

The idea of carrying out the preparation of (meth)acrylic acid by heterogeneously catalyzed gas phase partial oxidation of at least one saturated hydrocarbon precursor compound in a structured catalyst bed is known in abstract form from Catalysis Letters Vol. 87, Nos. 3–4, April 2003, p. 195 to 199. However, a disadvantage of this publication is that it makes no disclosure on the type and manner of the structuring.

Such a structured charge used in EP-A 1193240 is, for example, one whose catalysts are exclusively those whose active composition is at least one multimetal oxide I, and the volume concentration of these catalysts I increases in the flow direction of the reaction gas mixture.

The documents EP-A 575897, DE-A 3300044, DE-A 19855913, DE-A 10046957, DE-A 19948523, DE-A 44070202 and DE-A 10101695 disclose catalysts whose active composition is a multimetal oxide II. These documents recommend such catalysts for the catalytic partial oxidation in the gas phase of propene to acrolein and also of isobutene or tert-butanol to methacrolein.

DE-A 10118814 also recommends multimetal oxide I active compositions as catalysts for the heterogeneously catalyzed gas phase partial oxidation of propene to acrylic acid, and DE-A 10261186 recommends multimetal oxide I active compositions as catalysts for the heterogeneously catalyzed gas phase partial oxidation of acrolein to acrylic acid.

Among the catalysts I, preference is given for the process according to the invention to those whose active composition is at least one multimetal oxide I in whose X-ray diffractogram the intensity $P_i$ of the reflection i and the intensity $P_k$ of the reflection k fulfill the relationship $0.55 \leq R \leq 0.85$ in which R is the intensity ratio defined by the formula $$R = P_i/(P_i + P_k).$$

More preferably for R in the process according to the invention, 0.55 or $0.65 \leq R \leq 0.85$, or $0.67 \leq R \leq 0.75$, and most preferably, R=from 0.69 to 0.75 or R=from 0.71 to 0.74 or 0.73, or R=0.72.

In addition to the reflections h, i and k, the X-ray diffractogram of catalytically active multimetal oxides I which are suitable in accordance with the invention generally also contains further reflections whose peak locations are at the following reflection angles (2Θ):

9.0±0.4° (l),
6.7±0.4° (o) and
7.9±0.4° (p).

It is also favorable in accordance with the invention when the X-ray diffractogram additionally contains a reflection whose peak location is at the reflection angle (2Θ)=45.2±0.4° (q).

Frequently, the X-ray diffractogram of multimetal oxides I which are suitable in accordance with the invention also contains the reflections 29.2±0.4° (m) and 35.4±0.4° (n) (peak locations).

When the intensity of 100 is assigned to the reflection h, it is favorable in accordance with the invention when the reflections i, l, m, n, o, p, q in the same intensity scale have the following intensities:

i: from 5 to 95, frequently from 5 to 80, in some cases from 10 to 60;
l: from 1 to 30;
m: from 1 to 40;
n: from 1 to 40
o: from 1 to 30;
p: from 1 to 30 and
q: from 5 to 60.

When the X-ray diffractogram of the multimetal oxide active compositions I which are suitable in accordance with the invention contains of the aforementioned additional reflection, the half-height width-thereof is advantageously $\leq 1°$.

The specific surface area of multimetal oxide active compositions I which are suitable in accordance with the invention is favorably from 1 to 40 m²/g, advantageously from 10 or 11 or 12 to 40 m²/g and frequently from 15 or 20 to 40 or 30 m²/g (determined by the BET method, nitrogen).

Preference is given in accordance with the invention to the use of catalysts I whose active composition is at least one multimetal oxide I whose X-ray diffractogram has no reflection having the peak location 2Θ=50.0±0.3°. The structure of such multimetal oxides I is referred too as i phase. When the active multimetal oxide I has a reflection having the peak location 2Θ=50.0±0.3°, it generally contains a mixture of i and k phase (cf. DE-A 10118814 and DE-A 10261186).

All data relating to an X-ray diffractogram in this document relate to an X-ray diffractogram generated using Cu—Kα radiation as the X-ray radiation (Siemens Theta-Theta D-5000 diffractometer, tube voltage: 40 kV, tube current: 40 mA, aperture V20 (variable), collimator V20 (variable), secondary monochromator aperture (0.1 mm), detector aperture (0.6 mm), measuring interval (2Θ):0.02°, measuring time per step: 2.4 s, detector: scintillation counting tube; definition of the intensity of a reflection in the X-ray diffractogram relates in this document to the definition laid down in DE-A 19835247, DE-A 10122027, and also in DE-A 10051419 and DE-A 10046672; the same applies to the definition of the half-height width).

Irrespective of the specific X-ray diffractogram, particularly favorable catalytically active multimetal oxides I in accordance with the invention are those which satisfy the general stoichiometry C

$$Mo_1V_aM^1{}_bM^2{}_cM^3{}_dO_n \qquad (C)$$

where $M^1$=at least one of the elements from the group consisting of Te and Sb;
$M^2$=at least one of the elements from the group consisting of Nb, Ti, W, Ta and Ce;
$M^3$=at least one of the elements from the group consisting of Pb, Ni, Co, Bi, Pd, Ca, Mg, Fe, Mn, Ag, Pt, Cu, Au, Ga, Zn, Sn, In, Re, Ir, Sm, Sc, Y, Pr, Nd and Tb;
a=from 0.01 to 1,
b=from >0 to 1,
c=from >0 to 1,
d=from $\geq 0$ to 0.5 (preferably from >0 to 0.5) and
n=a number which is determined by the valency and frequency of the elements in (C) other than oxygen.

The stoichiometric coefficient a of the multimetal oxide active compositions (C), irrespective of the preferred ranges for the other stoichiometric coefficients of the active multimetal oxide compositions (C), is preferably from 0.05 to 0.6, more preferably from 0.1 to 0.6 or 0.5.

Irrespective of the preferred ranges for the other stoichiometric coefficients of the multimetal oxide active compositions (C), the stoichiometric coefficient b is preferably from 0.01 to 1, and more preferably from 0.01 or 0.05 or 0.1 to 0.5 or 0.4.

The stoichiometric coefficient c of multimetal oxide active compositions (C) which are advantageous in accordance with the invention, irrespective of the preferred ranges for the other stoichiometric coefficients of the multimetal oxide active compositions (C), is from 0.01 to 1 and more preferably from 0.01 or 0.05 or 0.1 to 0.5 or 0.4. A range for the stoichiometric coefficient c which is very particularly preferred in accordance with the invention and can be combined, irrespective of the preferred ranges for the other stoichiometric coefficients of the multimetal oxide active compositions (C) which are advantageously suitable in accordance with the invention, with all other preferred ranges of the multimetal oxide active compositions (C) in this document is the range from 0.05 to 0.2.

According to the invention, the stoichiometric coefficient d of the multimetal oxide active compositions (C), irrespective of the preferred ranges for the other stoichiometric coefficients of the multimetal oxide active compositions (C), is preferably from 0.00005 or 0.0005 to 0.5, more preferably from 0.001 to 0.5, frequently from 0.002 to 0.3 and often from 0.005 or 0.01 to 0.1.

Particularly favorable in accordance with the invention are multimetal oxide active compositions (C) whose stoichiometric coefficients a, b, c and d are simultaneously within the following framework:
a=from 0.05 to 0.6;
b=from 0.01 to 1 (or from 0.01 to 0.5);
c=from 0.01 to 1 (or from 0.01 to 0.5); and
d=from 0.0005 to 0.5 (or from. 0.001 to 0.3).

Very particularly favorable in accordance with the invention-are multimetal oxide active compositions (C) whose stoichiometric coefficients a, b, c and d are simultaneously within the following framework:
a=from 0.1 to 0.6;
b=from 0.1 to 0.5;
c=from 0.05 or 0.1 to 0.5; and
d=from 0.001 to 0.5, or from 0.002 to 0.3, or from 0.005 to 0.1.

$M^1$ is preferably Te.

All of the aforementioned is true in particular when at least 50 mol % of the total amount of $M^2$ is Nb and most preferably when at least 75 mol % of the total amount of $M^2$, or 100 mol % of the total amount of $M^2$, is Nb.

It is also true in particular, irrespective of the definition of $M^2$, when $M^3$ is at least one element from the group consisting of Pt, Fe, Re, Mn, Cu, Ni, Co, Bi, Pd, Ag, Au, Pb and Ga, or at least one element from the group consisting of Ni, Co, Pd, Pt, Fe and Bi.

All of the aforementioned is also true in particular when at least 50 mol % of the total amount of $M^2$, or at least 75 mol %, or 100 mol %, is Nb, and $M^3$ is at least one element from the group consisting of Pt, Fe, Re, Mn, Cu, Ni, Co, Bi, Pd, Ag, Au, Pb and Ga.

All of the aforementioned is also true in particular when at least 50 mol %, or at least 75 mol %, or 100 mol %, of the total amount of $M^2$ is Nb, and $M^3$ is at least one element from the group consisting of Ni, Co, Pd, Pt, Fe and Bi.

Very particular preference is given to all statements regarding the stoichiometric coefficients applying when $M^1$=Te, $M^2$=Nb and $M^3$=at least one element from the group consisting of Ni, Co, Pt and Pd.

The preparation of multimetal oxide active compositions I which are suitable in accordance with the invention, especially those of the stoichiometry C, may be effected by preparative processes described in the prior art (cf., for example, DE-A 19835247, EP-A 529853, EP-A 603836, EP-A 608838, EP-A 895809, EP-A 962253, EP-A 1080784, EP-A 1090684, EP-A 1123738, EP-A 1192987, EP-A 1192986, EP-A 1192982, EP-A 1192983 and EP-A 1192988).

In these processes, a very intimate, preferably finely divided, dry mixture is generated from suitable sources of the elemental constituents of the multimetal oxide composition and thermally treated at temperatures of from 350 to 700° C. or from 400 to 650° C. or from 400 to 600° C. The thermal treatment may in principle be-effected either under an oxidizing, a reducing- or under an inert atmosphere. A useful oxidizing atmosphere is, for example, air, air enriched with molecular oxygen or air depleted in oxygen. However, preference is given to carrying out the thermal treatment under an inert atmosphere, i.e., for example, under molecular nitrogen and/or noble gas. Typically, the thermal treatment is effected at atmospheric pressure (1 atm). It will be appreciated that the thermal treatment may also be effected under reduced pressure or under elevated pressure.

When the thermal treatment is effected under a gaseous atmosphere, it may either be stationary or flow. It preferably flows. Overall, the thermal treatment may take up to 24 h or more.

Preference is given to effecting the thermal treatment initially under an oxidizing oxygen-containing) atmosphere (for example under air) at a temperature of from 150 to 400° C. or from 250 to 350° C. (=predecomposition step). Afterward, the thermal treatment is appropriately continued under inert gas at temperatures of from 350 to 700° C. or from 400 to 650° C. or from 450 to 600° C. It will be appreciated that the thermal treatment may also be effected in such a way that the multimetal oxide precursor composition, before its thermal treatment, is initially (optionally after pulverization) tableted (optionally with the addition of from 0.5 to 2% by weight of finely divided graphite), then thermally treated and subsequently spalled again.

The intimate mixing of the starting compounds may be effected in dry or in wet form.

When it is effected in dry form, the starting compounds are appropriately used as finely divided powder and, after the mixing and any compaction, subjected to calcination (thermal treatment).

However, preference is given to effecting the intimate mixing in wet form. Typically, the starting compounds are mixed together in the form of an aqueous solution (optionally with the use of complexing agents; cf., for example, DE-A 10145958) and/or suspension. Subsequently, the aqueous composition is dried and calcined after the drying. Appropriately, the aqueous composition is an aqueous solution or an aqueous suspension. Preference is given to effecting the drying process directly after the preparation of the aqueous mixture (especially in the case of an aqueous solution; cf., for example, JP-A 7-315842) and by spray drying (the exit temperatures are generally from 100 to 150° C.; the spray drying may be carried out in cocurrent or in countercurrent), which results in a particularly intimate dry mixture, in particular when the aqueous composition to be spray-dried is an aqueous solution or suspension. However, it may also be dried by concentrating by evaporation under reduced pressure, by freeze-drying or by conventional concentration by evaporation.

Useful sources for the elemental constituents when carrying out the above-described preparation method are all of those which are capable of forming oxides and/or hydroxides on heating (optionally under air). It will be appreciated that such starting compounds may also already partly or exclusively be oxides and/or hydroxides of the elemental constituents. In other words, useful starting compounds are especially all of those mentioned in EP-A 1254707, EP-A 1254709 and EP-A 1192987.

Suitable sources for the element Mo are, for example, molybdenum oxides such as molybdenum trioxide, molybdates such as ammonium heptamolybdate tetrahydrate and molybdenum halides such as molybdenumm chloride.

Suitable starting compounds for the element V are, for example, vanadium oxysulfate hydrate, vanadyl acetylacetonate, vanadates such as ammonium metavanadate, vanadium oxides such as vanadium pentoxide ($V_2O_5$), vanadium halides such as vanadium tetrachloride ($VCl_4$) and vanadium oxyhalides such as $VOCl_3$. The vanadium starting compounds used may also be those which contain the vanadium in the +4 oxidation state.

Suitable sources for the element tellurium are tellurium oxides such as tellurium dioxide, metallic tellurium, tellurium halides such as $TeCl_2$, but also telluric acids such as orthotelluric acid $H_6TeO_6$.

Advantageous antimony starting compounds are antimony halides such as $SbCl_3$, antimony oxides such as antimony trioxide ($Sb_2O_3$), or antimony trioxide pretreated with $H_2O_2$, antimony acids such as $HSb(OH)_6$, but also antimony oxide salts such as antimony oxide sulfate $(SbO)_2SO_4$ and antimony acetate.

Suitable niobium sources are, for example, niobium oxides such as niobium pentoxide ($Nb_2O_5$), niobium oxide halides such as $NbOCl_3$, niobium halides such as $NbCl_5$, but also complexes of niobium and alcohols (e.g. ethanol, n-propanol), organic carboxylic acids and/or dicarboxylic acids, for example oxalates and alkoxides. It will be appreciated that useful niobium sources are also the Nb-containing solutions used in EP-A 895 809.

With regard to all other possible elements (in particular Pb, Ni, Cu, Co, Bi and Pd), suitable starting compounds are in particular their halides, nitrates, formates, oxalates, acetates, carbonates and/or hydroxides. Suitable starting compounds are in many cases also their oxo compounds, for example tungstates or acids derived from them. The starting compounds used are frequently also ammonium salts.

Useful starting compounds are also polyanions of the Anderson type, as described, for example, in Polyhedron Vol. 6, No. 2, pp. 213–218, 1987. A further suitable literature source for polyanions of the Anderson type is Kinetics and Catalysis, Vol. 40, No. 3, 1999, pp 401 to 404.

Other polyanions suitable as starting compounds are, for example, those of the Dawson or Keggin type. Preference is given to using those starting compounds which are converted to their oxides at elevated temperatures, either in the presence or with the exclusion of oxygen, in some cases with the release of gaseous compounds.

The procedure described generally provides an intimate mixed crystal system composed of i phase and k phase. In this mixture, the fraction of i phase may be increased or isolated by washing out the k phase to the desired extent using suitable liquids (washing generally changes the stoichiometry only insignificantly). Useful such liquids are, for example, organic acids and aqueous solutions of organic acids (e.g. oxalic acid, formic acid, citric acid and tartaric acid), inorganic acids (e.g. nitric acid), aqueous solutions of inorganic acids (e.g. aqueous telluric acid or aqueous nitric acid), alcohols and aqueous hydrogen peroxide solutions. Likewise suitable is the washing process of EP-A 1254707 and of EP-A 1254706.

An increased fraction of i phase (and in favorable cases substantially pure i phase) is generally attained directly in the preparation of multimetal oxides I (or C) when they are prepared by a hydrothermal route, as described, for example, in DE-A 10029338, DE-A 10254278 and JP-A 2000-143244.

However, active multimetal oxide compositions (C) where d>0 which are suitable in accordance with the invention may also be prepared by initially generating a multimetal oxide (C') which differs from a multimetal oxide C only in that d=0.

Such a preferably finely divided multimetal oxide composition C' may then be saturated with solutions (for example aqueous) of elements $M^3$ (for example by spraying), subsequently dried (preferably at temperatures $\leq 100°$ C.) and then, as already described for the preparation of multimetal oxides 1, calcined (preferably in an inert gas stream; preference is given here to dispensing with predecomposition under air). The use of aqueous nitrate and/or halide solutions of elements $M^3$ and/or the use of aqueous solutions in which the elements $M^3$ are complexed with organic compounds (for example acetates or acetylacetonates) is particularly advantageous for this preparative variant.

The active multimetal oxides I which are suitable in accordance with the invention and obtainable as described, in particular those of the stoichiometry (C), may be used in the process according to the invention as such [for example as a powder or after tableting the powder (frequently with the addition of from 0.5 to 2% by weight of finely divided graphite) and subsequent spalling to give spall comminuted] or may be used as catalysts I for the process according to the invention shaped to shaped bodies. The at least one catalyst bed I may be a fixed bed, a moving bed or a fluidized bed.

The shaping to shaped bodies may be effected, for example, by applying to a support body, as described in DE-A 10118814, or WO 02/83615, or DE-A 10051419. The procedure may also correspond to that of DE-A 4442346.

The support bodies to be used for the active multimetal oxide compositions 1, especially those of the general formula (C), which are suitable according to the invention are preferably chemically inert. In other words, they essentially do not intervene in the course of the heterogeneously catalyzed gas phase partial oxidation according to the invention.

According to the invention, useful materials for the support bodies are in particular aluminum oxide, silicon dioxide, silicates such as clay, kaolin, steatite (preferably having a low water-soluble alkali content and also preferably from Ceramtec in Germany, for example steatite C220), pumice, aluminum silicate and magnesium silicate, silicon carbide, zirconium dioxide and thorium dioxide.

The surface of the support body may be either smooth or rough. Advantageously, the surface of the support body is rough, since increased surface roughness generally results in increased adhesion of the applied active composition coating.

Frequently, the surface roughness $R_z$ of the support body is in the range from 5 to 200 μm, often in the range from 20 to 100 μm (determined according to DIN 4768 sheet 1 using a "Hommel tester for DIN-ISO surface parameters" from Hommelwerke, Germany).

In addition, the support material may be porous or nonporous. Appropriately, the support material is nonporous (total volume of the pores based on the volume of the support body $\leq 1\%$ by volume).

The thickness of the active oxide composition coating on the coated catalysts is typically from 10 to 1000 μm.

However, it may also be from 50 to 700 µm, from 100 to 600 µm or from 150 to 400 µm. Possible coating thicknesses are also from 10 to 500 µm, from 100 to 400 µm or from 150 to 300 µm.

In principle, any geometries of the support bodies are useful for the process according to the invention. Their longest dimension is generally from 1 to 10 mm. However, preference is given to using spheres or cylinders, in particular hollow cylinders, as support bodies. Favorable diameters for support spheres are from 1.5 to 5 mm. When cylinders are used as support bodies, their length is preferably from 2 to 10 mm and their external diameter is preferably from 4 to 10 mm. In the case of rings, the wall thickness is additionally typically from 1 to 4 mm. Annular support bodies which are suitable in accordance with the invention may also have a length of from 3 to 6 mm, an external diameter of from 4 to 8 mm and a wall thickness of from 1 to 2 mm. However, a support ring geometry of 7 mm×3 mm×4 mm or of 5 mm×3 mm×2 mm (external diameter×length×internal diameter) is also possible.

Such coated catalysts may be prepared in the simplest manner, for example, in such a way that multimetal oxide active compositions I, in particular those of the general formula (C), are preformed, they are converted to finely divided form and finally applied to the surface of the support body with the aid of a liquid binder. To this end, the surface of the support body is, in the simplest manner, moistened with the liquid binder and a layer of the active composition is attached to the moistened surface by contacting with the finely divided active composition, for example that of the general formula (C). Finally, the coated support body is dried. It will be appreciated that the procedure may be repeated periodically to achieve an increased layer thickness. In this case, the coated basic body becomes the new "support body", etc. On completion of coating, calcination may be effected once again under the conditions already specified (preferably again under inert gas).

The fineness of the catalytically active multimetal oxide compositions I to be applied to the surface of the support body, for example that of the general formula (C), is of course adapted to the desired coating thickness. Suitable for the coating thickness range of from 100 to 500 µm are, for example, those active composition powders of which at least 50% of the total number of powder particles pass through a sieve of mesh width from 1 to 20 µm and whose numerical fraction of particles having a longest dimension of above 50 mm is less than 10%. In general, the distribution of the longest dimensions of the powder particles, as a result of the preparation, corresponds to a Gaussian distribution. Frequently, the particle size distribution is as follows:

For a performance of the coating process described on the industrial scale, it is recommended, for example, to employ the process principle disclosed in DE-A 2909671, and also in DE-A 10051419. In other words, the support bodies to be coated are initially charged in a preferably inclined (the inclination angle is generally $\geq 0°$ and $\leq 90°$, usually $\geq 30°$ and $\leq 90°$; the inclination angle is the angle of the central axis of the rotating vessel relative to the horizontal) rotating vessel (for example rotary pan or coating drum). The rotating vessel conducts the, for example, spherical or cylindrical support bodies under two metering devices arranged successively in a certain separation. The first of the two metering devices appropriately corresponds to a nozzle (for example an atomizer nozzle operated with compressed air), which sprays the support bodies rolling in the rotary pan with the liquid binder and moistens them in a controlled manner. The second metering device is outside the atomization cone of the sprayed liquid binder and serves to feed the finely divided oxidic active composition (for example via an agitated channel or a powder screw). The support spheres which have been moistened in a controlled manner take up the active composition powder supplied, which is compressed by the rolling motion to a continuous coating on the outer surface of the, for example, cylindrical or spherical support body.

If required, the support body basically coated in this way, in the course of the subsequent rotation, again passes through the spray nozzles, and is moistened in a controlled manner, in order, in the course of the further motion, to be able to take up a further layer of finely divided oxidic active composition, etc. (intermediate drying is generally not necessary). Finely divided oxidic active composition and liquid binder are generally supplied continuously and simultaneously.

The liquid binder may be removed on completion of coating, for example by the action of hot gases such as $N_2$ or air. Remarkably, the coating process described brings about fully satisfactory adhesion of the successive layers both to each other and to the base layer on the surface of the support body.

It is essential for the above-described coating method that the moistening of the surface of the support body to be coated is carried out in a controlled manner. In short, this means that the support surface is appropriately moistened in such a way that, although it has adsorbed liquid binder, no liquid phase as such visibly appears on the support surface. When the support body surface is too moist, the finely divided catalytically active oxide composition agglomerates to separate agglomerates, instead of adhering to the surface.

| D (µm) | 1 | 1.5 | 2 | 3 | 4 | 6 | 8 | 12 | 16 | 24 | 32 | 48 | 64 | 96 | 128 |
|---|---|---|---|---|---|---|---|---|---|---|---|---|---|---|---|
| x | 80.5 | 76.3 | 67.1 | 53.4 | 41.6 | 31.7 | 23 | 13.1 | 10.8 | 7.7 | 4 | 2.1 | 2 | 0 | 0 |
| y | 19.5 | 23.7 | 32.9 | 46.6 | 58.4 | 68.3 | 77 | 86.9 | 89.2 | 92.3 | 96 | 97.9 | 98 | 100 | 100 |

In this table:
D = diameter of the particle,
x = the percentage of the particles whose diameter is $\geq$ D; and
y = the percentage of the particles whose diameter is < D.

In this table:
D=diameter of the particle,
x=the percentage of the particles whose diameter is $\geq$D; and
y=the percentage of the particles whose diameter is <D.

Detailed information on this subject can be found in DE-A 2909671 and in DE-A 10051419.

The aforementioned final removal of the liquid binder used can be carried out in a controlled manner, for example by evaporation and/or sublimation. In the simplest case, this may be effected by the action of hot gases at appropriate temperature (frequently from 50 to 300° C., frequently 150° C.). However, the action of hot gases may also be used only to bring about predrying. The final drying may then be effected, for example, in a drying oven of any type (for example belt dryer) or in the reactor. The action temperature should not be above the calcination temperature employed to prepare the oxidic active composition. It will be appreciated that the drying may also be carried out exclusively in a drying oven.

The binder used for the coating process, irrespective of the type and the geometry of the support body, may be: water, monohydric alcohols such as ethanol, methanol, propanol and butanol, polyhydric alcohols such as ethylene glycol, 1,4-butanediol, 1,6-hexanediol or glycerol, mono- or polybasic organic carboxylic acids such as propionic acid, oxalic acid, malonic acid, glutaric acid or maleic acid, amino alcohols such as ethanolamine or diethanolamine, or else mono- or polyhydric organic amides such as formamide. Suitable binders are also solutions consisting of from 20 to 90% by weight of water and from 10 to 80% by weight of an organic compound dissolved in water whose boiling point or sublimation temperature at atmospheric pressure (1 atm) is >100° C., preferably >150° C. Advantageously, the organic compound is selected from the above listing of possible organic binders. The organic fraction of the aforementioned aqueous binder solutions is preferably from 10 to 50% by weight and more preferably from 20 to 30% by weight. Useful organic components are also monosaccharides and oligosaccharides such as glucose, fructose, sucrose or lactose, and also polyethylene oxides and polyacrylates.

It is significant that such coated catalysts can be prepared not only by applying the finished, finely ground active multimetal oxide compositions I, for example of the general formula (C), to the moistened support body surface.

Rather, instead of the active oxide composition, a finely divided precursor composition thereof may also be applied to the moistened support surface (employing the same coating process and binder) and the calcination carried out after drying the coated support body (support bodies may also be impregnated with a precursor solution, subsequently dried and then calcined). Finally, the k phase different to the i phase may be washed out if required. Subsequently, calcination may be repeated in the manner described.

Such a finely divided precursor composition may be, for example, that composition which is obtainable by initially generating a very intimate, preferably finely divided dry mixture from the sources of the elemental constituents of the desired active multimetal oxide composition I to be used in accordance with the invention, for example that of the general formula (C) (for example by spray drying an aqueous suspension or solution of the sources), and thermally treating this finely divided dry mixture (optionally after tableting with the addition of from 0.5 to 2% by weight of finely divided graphite) at a temperature of from 150 to 350° C., preferably from 250 to 350° C., under an oxidizing (oxygen-containing) atmosphere (for example under air) (for a few hours) and finally, if required, subjecting it to grinding.

After the coating of the support bodies with the precursor composition, calcination is then effected, preferably under an inert gas atmosphere (all other atmospheres are also possible), at temperatures of from 360 to 700° C. or from 400 to 650° C. or from 400 to 600° C.

It will be appreciated that active multimetal oxide compositions I which can be used in accordance with the invention, for example those of the general formula (C), may also be shaped by extrusion and/or tableting, either of finely divided multimetal oxide active composition I or of finely divided precursor composition of a multimetal oxide active composition I (if necessary, the phases other than the i phase may finally be washed out, optionally including a recalcination).

Useful geometries are spheres, solid cylinders and hollow cylinders (rings). The longest dimension of the aforementioned geometries is generally from 1 to 10 mm. In the case of cylinders, their length is preferably from 2 to 10 mm and their external diameter is preferably from 4 to 10 mm. In the case of rings, the wall thickness is additionally typically from 1 to 4 mm. Annular unsupported catalysts suitable according to the invention may also have a length of from 3 to 6 mm, an external diameter of from 4 to 8 mm and a wall thickness of from 1 to 2 mm. However, an unsupported catalyst ring geometry of 7 mm×3 mm×4 mm or of 5 mm×3 mm×2 mm (external diameter×length×internal diameter) is also possible.

The geometries of the multimetal oxide active compositions I to be used for the process according to the invention, in particular those of the general formula (C), may of course also be all of those of DE-A 10101695.

It is essential to the invention, as already stated, that the multimetal oxide active compositions I to be used in accordance with the invention, in particular those of the general formula C, have an X-ray diffractogram (in this document always based on Cu—Kα radiation) which has reflections h, i and k whose peak locations are at the reflection angles (2Θ) of 22.2±0.5° (h), 27.3±0.5° (i) and 28.2±0.5° (k), the reflection h being the most intensive within the X-ray diffractogram, and also having a half-height width of at most 0.5°, and the half-height width of the reflection i and of the reflection k each being $\leq 1°$.

At the same time, the X-ray diffractogram should more preferably have no reflection having the peak location 2Θ=50±0.3°.

In this document, the definition of the intensity of a reflection in the X-ray diffractogram relates, as already stated, to the definition laid down in DE-A 19835247, and also in DE-A 10051419 and DE-A 10046672.

In other words, if $A^1$ denotes the peak location of a reflection 1 and $B^1$, in the line of the X-ray diffractogram viewed along the intensity axis at right angles to the 2Θ axis, denotes the next pronounced minimum (minima having reflection shoulders are not taken into account) to the left of the peak location $A^1$ and $B^2$ is correspondingly the next pronounced minimum to the right of the peak location $A^1$ and $C^1$ denotes the point at which a straight line drawn from the peak location $A^1$ at right angles to the 2Θ axis cuts a straight line joining the points $B^1$ and $B^2$, the intensity of the reflection 1 is the length of the straight line section $A^1C^1$ which then extends from the peak location $A^1$ to the point $C^1$. The expression minimum in this context means a point at which the slope of a tangent to the curve in a base region of the reflection 1 changes from a negative value to a positive value, or a point at which the slope tends to zero, using the coordinates of the 2Θ axis and of the intensity axis for the determination of the slope.

In this document, the half-height width is correspondingly the length of the straight line section between the two intersection points $H^1$ and $H^2$ when a line is drawn parallel to the 2Θ axis in the middle of the straight line section $A^1C^1$, $H^1$, $H^2$ meaning in each case the first point at which these parallel lines cut the line as defined above of the X-ray diffractogram to the left and right of $A^1$.

An exemplary execution of the determination of half-height width and intensity is also shown by FIG. 6 in DE-A 10046672.

It will be appreciated that the multimetal oxide active compositions I to be used in accordance with the invention, in particular those of the general formula (C), may also be used as catalytic active compositions diluted with finely divided, for example colloidal, materials such as silicon dioxide, titanium dioxide, aluminum oxide, zirconium oxide, niobium oxide.

The dilution composition ratio may be up to 9 (diluent):1 (active composition). In other words, possible diluent composition ratios are, for example, 6 (diluent):1 (active composition) and 3 (diluent):1 (active composition). The diluent may be incorporated before and/or after the calcination, generally even before the drying. It is normally effected before the shaping.

When the incorporation is effected before the drying or before the calcination, the diluent has to be selected in such a way that it is substantially preserved in the fluid medium or in the calcination. This is generally the case, for example, for oxides calcined at appropriately high temperatures.

Advantageously in accordance with the invention, the active composition of catalysts I has a specific surface area O of from 1 to 40 m²/g, advantageously from 10, or 11, or 12 to 40 m²/g and frequently from 15 or 20 to 40 or 30 m²/g, and a total pore volume of from 0.1 to 1, frequently from 0.2 to 0.8 and in many cases from 0.3 to 0.7, cm³/g.

The different pore diameters generally contribute to the total pore volume as follows:

pores having a diameter in the range of <0.03 µm: ≦10% by volume, frequently ≦5% by volume;

pores having a diameter in the range from ≧0.03 to ≦0.3 µm: from 5 to 40% by volume, frequently from 15 to 30% by volume;

pores having a diameter in the range from >0.3 to ≦10 µm: from 30 to 70% by volume, frequently from 40 to 60% by volume; and pores having a diameter in the range of >10 µm: ≦30% by volume, frequently from 5 to 25% by volume.

The pore diameter which makes the greatest contribution to the total pore volume is generally in the range from 0.3 to 6 µm. The aforementioned is especially true in the case of coated catalysts.

All data in this document on determinations of specific surface areas and also micropores relate to determinations to DIN 66131 (Brunauer-Emmet-Teller (BET) determination of the specific surface area of solids by gas adsorption ($N_2$)).

All data in this document on determinations of total pore volumes and also of diameter distributions on these total pore volumes relate, unless stated otherwise, to determinations by the mercury porosymetry method using the Auto Pore 9220 instrument from Micromeritics GmbH, 4040 Neuss, Germany (belt width from 30 Å to 0.3 mm).

Regarding the active compositions of the stoichiometry of the general formula A, the stoichiometric coefficient b is preferably from 2 to 4, the stoichiometric coefficient c is preferably from 3 to 10, the stoichiometric coefficient d is preferably from 0.02 to 2, the stoichiometric coefficient e is preferably from 0 to 5 and the stoichiometric coefficient a is preferably from 0.4 to 2. The stoichiometric coefficient f is advantageously from 0.5 or 1 to 10. More preferably, the aforementioned stoichiometric coefficients are simultaneously within the preferred ranges mentioned.

In addition, $X^1$ is preferably cobalt, $X^2$ is preferably K, Cs and/or Sr, more preferably K, $X^3$ is preferably zinc and/or phosphorus and $X^4$ is preferably Si. More preferably, the variables $X^1$ to $X^4$ are simultaneously defined above.

More preferably, all stoichiometric coefficiencts a to f and all variables $X^1$ to $X^4$ are simultaneously each as advantageously defined above.

Within the stoichiometries of the general formula B, preference is given to those which correspond to the general formula D

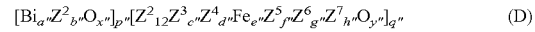

(D)

where
$Z^2$=molybdenum or molybdenum and tungsten,
$Z^3$=nickel and/or cobalt, preferably Ni,
$Z^4$=thallium, an alkali metal and/or an alkaline earth metal, preferably K, Cs and/or Sr,
$Z^5$=phosphorus, arsenic, boron, antimony, tin, cerium and/or $B^1$,
$Z^6$=silicon, aluminum, titanium and/or zirconium, preferably Si,
$Z^7$=copper, silver and/or gold,
a"=from 0.1 to 1,
b"=from 0.2 to 2,
c"=from 3 to 10,
d"=from 0.02 to 2,
e"=from 0.01 to 5, preferably from 0.1 to 3,
f"=from 0 to 5,
g"=from 0 to 10, preferably from >0 to 10, more preferably from 0.2 to 10 and most preferably from 0.4 to 3,
h"=from 0 to 1,
x", y"=numbers determined by the valency and frequency of the elements in III other than oxygen and
p", q"=numbers whose p"/q" ratio is from 0.1 to 5, preferably from 0.5 to 2.

In addition, preference is given in accordance with the invention to active compositions of the stoichiometry B which contain three-dimensional regions of the chemical composition $Y^1{}_a Y^2{}_b O_{x'}$ which are delimited from their local environmental as a consequence of their different composition from their local environment and whose longest diameter (longest line passing through the center of the region and connecting two points on the surface (interface) of the region) is from 1 nm to 100 µm, frequently from 10 nm to 500 nm or from 1 µm to 50 or 25 µm.

Active compositions of the stoichiometry B obtainable particularly advantageously in accordance with the invention are those in which $Y^1$ is only bismuth.

Within the active compositions of the stoichiometry D, preference is given in accordance with the invention to those in which $Z^2{}_{b''}$=(tungsten)$_{b''}$ and $Z^2{}_{12}$=(molybdenum)$_{12}$.

In addition, preference is given in accordance with the invention to active compositions of the stoichiometry D which contain three-dimensional regions of the chemical composition $Bi_{a''}Z^2{}_{b''}O_{x''}$ which are delimited from their local environment as a consequence of their different composition from their local environment and whose longest diameter (longest line passing through the center of the region and connecting two points on the surface (interface) of the region) is from 1 nm to 100 µm, frequently from 10 nm to 500 nm or from 1 µm to 50 or 25 µm.

In addition, it is advantageous when at least 25 mol % (preferably at least 50 mol % and more preferably at least 100 mol %) of the total $[Y^1{}_a Y^2{}_b O_{x'}]_p$ ($[Bi_{a''}Z^2{}_{b''}O_{x''}]_{p''}$) fraction of the active compositions of the stoichiometry B (active compositions of the stoichiometry D) obtainable in accordance with the invention in the active compositions of the stoichiometry B (active compositions of the stoichiometry D) obtainable in accordance with the invention is in the form of three-dimensional regions of the chemical composition $Y^1{}_{a'}Y^2{}_{b'}O_{x'}$ ($[Bi_{a''}Z^2{}_{b''}O_{x''}]$) which are delimited from their local environment as a consequence of their different chemical composition to their local environment and whose longest diameter is in the range from 1 nm to 100 μm.

Processes for preparing multimetal oxides II are described, for example, in EP-A 184790, EP-A 575897, DE-A 3300044, DE-A 19855913, DE-A 10046957, WO 02/24620, DE-A 10048523, DE-A 44070202, DE-A 10101695 and in DE-A 10121592.

They are customarily shaped in bulk to give spheres, rings or cylinders or used in the form of coated catalysts, i.e. preshaped inert support bodies coated with the active composition. However, it will be appreciated that they may also be used in powder form as catalysts II. It will be appreciated that the catalyst II used may also be the multimetal oxide catalyst ACS-4 from Nippon Shokubai comprising Bi, Mo and Fe.

In principle, active compositions A, B suitable for catalysts II can be prepared in a simple manner by generating a very intimate, preferably finely divided dry mixture having a composition corresponding to its stoichiometry from suitable sources of its elemental constituents and calcining it at temperatures of from 350 to 650° C. The calcination may be effected either under inert gas or under an oxidative atmosphere, for example air (mixture of inert gas and oxygen), or under a reducing atmosphere (for example a mixture of inert gas, $NH_3$, CO and/or $H_2$). The calcination time may be from a few minutes to a few hours and customarily falls with temperature. Useful sources of the elemental constituents of the multimetal oxide active compositions A, B include those compounds which are already oxides and/or those compounds which can be converted to oxides by heating, at least in the presence of oxygen.

In addition to the oxides, other useful starting compounds are in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which can decompose and/or fall apart on subsequent calcining at the latest to give compounds released in gaseous form may additionally be incorporated in the intimate dry mixture).

The intimate mixing of the starting compounds for preparing multimetal oxide active compositions A, B may be effected in dry or wet form. Where it is effected in dry form, the starting compounds are advantageously used as finely divided powders and subjected to calcination after mixing and optionally compacting. However, preference is given to effecting the intimate mixing in wet form. Customarily, the starting compounds are mixed with each other in the form of an aqueous solution and/or suspension.

Particularly intimate dry mixtures are obtained in the mixing process described when the starting materials are exclusively sources of the elemental constituents present in dissolved form. The solvent used is preferably water. The aqueous composition obtained is then dried, and the drying procedure is preferably effected by spray drying the aqueous mixture at exit temperatures of from 100 to 150° C.

The multimetal oxide compositions A, B suitable for catalysts II to be used in accordance with the invention may be used for the process according to the invention either in powder form or shaped into certain catalyst II geometries, in which case the shaping may be effected before or after the final calcination. For example, unsupported catalysts may be prepared from the powder form of the active composition or its uncalcined and/or partially calcined precursor composition by compacting to the desired catalyst geometry (for example by tableting, extruding or pressing to give strands), in the course of which assistants, for example graphite or stearic acid as lubricants and/or shaping assistants and reinforcing agents such as microfibers of glass, asbestos, silicon carbide or potassium titanate, may optionally be added. Examples of useful unsupported catalyst geometries include solid cylinders or hollow cylinders having an external diameter and a length of from 2 to 10 mm. In the case of the hollow cylinders, a wall thickness of from 1 to 3 mm is appropriate. It will be appreciated that the unsupported catalyst may also have spherical geometry, in which case the sphere diameter may be from 2 to 10 mm.

It will be appreciated that the pulverulent active composition or its pulverulent precursor composition which has as yet only been partially calcined, if at all, may also be shaped by applying to preshaped inert catalyst supports. The coating of the support bodies for preparing the coated catalysts is generally performed in a suitable rotatable vessel, as disclosed, for example, in DE-A 2909671, EP-A 293859 or EP-A 714700. To coat the support bodies, the pulverulent composition to be applied is appropriately moistened and dried again after application, for example by means of hot air. The layer thickness of the pulverulent composition applied to the support bodies is appropriately selected within the range from 10 to 1 000 μm, preferably within the range from 50 to 500 μm and more preferably within the range from 150 to 250 μm.

Useful support materials may be customary porous or nonporous aluminum oxides, silicon dioxide, thorium dioxide, zirconium dioxide, silicon carbide or silicates such as magnesium or aluminum silicate. They generally behave substantially inertly with respect to the target reaction which underlies the process according to the invention. The support bodies may have a regular or irregular shape, although preference is given to regularly shaped support bodies having distinct surface roughness, for example spheres or hollow cylinders. The use of substantially nonporous, spherical supports having surface roughness and made of steatite whose diameter is from 1 to 8 mm, preferably from 4 to 5 mm, is suitable. However, useful support bodies are also cylinders whose length is from 2 to 10 mm and whose external diameter is from 4 to 10 mm. In the case of rings suitable as support bodies according to the invention, the wall thickness is further customarily from 1 to 4 mm. Annular support bodies to be used with preference according to the invention have a length of from 2 to 6 mm, an external diameter of from 4 to 8 mm and a wall thickness of from 1 to 2 mm. In particular, rings of geometry 7 mm □ 3 mm □ 4 mm (external diameter □ length □ internal diameter) are also suitable as support bodies according to the invention. It will be appreciated that the fineness of the catalytically active oxide compositions to be applied to the surface of the support body is adapted to the desired coating thickness (cf. EP-A 714 700).

Especially for preparing active compositions of the stoichiometry of the general formula B or D, it is advantageous to preform a mixed oxide $Y^1{}_{a'}Y^2{}_{b'}O_{x'}$ or $Bi_{a''}Z^2{}_{b''}O_{x''}$ as the source of the elements $Y^1$, $Y^2$ and Bi, $Z^2$ respectively in the absence of the remaining constituents of the active compositions of the stoichiometry of the general formula B or D and thus, after its preformation, as already described, to generate a finely divided shapeable mixture using sources of the remaining constituents of the active compositions of the stoichiometry of the general formula B or D, in order to form therefrom, optionally after adding shaping and/or reinforcing assistants, annular shaped unsupported catalyst precursor bodies and finally to convert them to annular unsupported catalysts by thermal treatment (calcination) as described.

The procedure may be as described in DE-A 10101695 or DE-A 10121592. However, the finely divided shapeable mixture should preferably be completed (compressed) in such a way that the side crushing strength of the resulting annular shaped unsupported catalyst precursor bodies is $\geq 12$ N and $\leq 23$ N, preferably $\geq 13$ N and $\leq 22$ N and more preferably $\geq 15$ N and $\leq 20$ N.

In the case that the preparation of the finely divided shapeable mixture is effected in wet form (in suspension), care has to be taken that the preformed mixed oxides $Y^1{}_a Y^2{}_b O_{x'}$ or $Bi_{a''} Z^2{}_{b''} O_{x''}$ do not go into solution to a significant extent.

A preparation method as described above also is described in detail, inter alia, in the documents DE-A 4407020, EP-A 835, EP-A 575897 and DE-C 3338380.

For example, water-soluble salts of $Y^1$ such as nitrates, carbonates, hydroxides or acetates may be mixed in water with $Y^2$ acids or their ammonium salts, the mixture dried (preferably spray-dried) and the dried composition subsequently thermally treated. The thermally treated composition is subsequently appropriately comminuted (for example in a ball mill or by jet milling) and, from the powder which generally consists of substantially spherical particles and is obtainable in this way, the particle class having a largest particle diameter lying within the largest diameter range desired for the active composition of the stoichiometry of the general formula B or D is separated by classification to be carried out in a manner known per se (for example wet or dry sieving) and is preferably mixed with, based on the mass of this separated particle class, preferably from 0.1 to 3% by weight of finely divided $SiO_2$ (the number-average largest particle diameter of the typically substantially spherical $SiO_2$ particles is appropriately from 10 to 50 nm), thus producing a starting composition 1. The thermal treatment is appropriately effected at temperatures of from 400 to 900° C., preferably from 600 to 900° C. The latter is especially true when the preformed mixed oxide is one of the stoichiometry $BiZ^2O_6$, $Bi_2Z^2{}_2O_9$ and/or $Bi_2Z^2{}_3O_{12}$, among which $Bi_2Z^2{}_2O_9$ is preferred, especially when $Z^2$=tungsten.

Typically, the thermal treatment is effected in an air stream (for example in a rotary tube furnace as described in DE-A 10325487). The duration of the thermal treatment generally extends to a few hours.

The remaining constituents of the desired active composition of the general formula B or D are normally used to prepare, starting from sources which are suitable in a manner known per se (cf. EP-A 835 and DE-C 3338380 and also DE-A 4407020), in an inventively appropriate manner, for example, a very intimate, preferably finely divided dry mixture (for example combine water-soluble salts such as halides, nitrates, acetates, carbonates or hydroxides in an aqueous solution and subsequently, for example, spray-dry the aqueous solution, or suspend water-insoluble salts, for example oxides, in aqueous medium and subsequently, for example, spray-dry the suspension) which is referred to here as starting composition 2. It is essential only that the constituents of the starting composition 2 are either already oxides or compounds which can be converted to oxides by heating, in the absence or presence of oxygen. Subsequently, the starting composition 1 and the starting composition 2 are mixed in the desired ratio in the inventive manner, optionally after adding shaping and/or reinforcing assistants, to give the mixture which can be shaped to the annular shaped unsupported catalyst precursor body. The shaping may, appropriately from an application point of view, be effected by an intermediate compaction stage.

In a less preferred embodiment, the preformed mixed oxide $Y^1{}_a Y^2{}_b O_{x'}$ or $Bi_{a''} Z^2{}_{b''} O_{x''}$ may also be intimately mixed with sources of the remaining constituents of the desired active composition in liquid, preferably aqueous, medium. This mixture is subsequently, for example, dried to give an intimate dry mixture and then, as already described, shaped and thermally treated. The sources of the remaining constituents may be dissolved and/or suspended in this liquid medium, whereas the preformed mixed oxide should be substantially insoluble, i.e. has to be suspended, in this liquid medium.

The preformed mixed oxide particles are present having a substantially unchanged longitudinal dimension established by the classification in the finished annular unsupported catalyst.

Preference is given in accordance with the invention to the specific surface area of mixed oxides $Y^1{}_a Y^2{}_b O_{x'}$ or $Bi_{a''} Z^2{}_{b''} O_{x''}$ preformed in this way being from 0.2 to 2 m$^2$/g, preferably from 0.5 to 1.2 m$^2$/g. In addition, the total pore volume of mixed oxides preformed in this way advantageously results predominantly from micropores.

Annular unsupported catalysts of this type obtained advantageously in accordance with the invention are those whose specific surface area O is from 5 to 20 or 15 m$^2$/g, frequently from 5 to 10 m$^2$/g. Their total pore volume is advantageously in the range from 0.1 to 1 or 0.8 cm$^3$/g, frequently in the range from 0.2 to 0.4 cm$^3$/g.

In contrast to the teaching of WO 03/039744 and to the teaching of EP-A 279374, the different pore diameters in such annular unsupported catalysts advantageously contribute to the total pore volume as follows:

Pores having a diameter in the range of <0.03 µm: ☐ 5% by volume;

Pores having a diameter in the range from ☐ 0.03 to ☐ 0.1 µm: ☐ 25% by volume;

Pores having a diameter in the range from >0.1 to <1 µm: ☐ 70% by volume and

Pores having a diameter in the range from ☐ 1 to ☐ 10 µm: ☐ 10% by volume.

In other words, in contrast to the teaching of EP-A 279374, the proportion of the pores having a diameter of ☐ 1 µm generally plays only a minor role in annular unsupported catalysts obtained in accordance with the invention.

In addition, the proportion of pores having a diameter in the range from ☐ 0.03 to ☐ 0.1 µm in annular unsupported catalysts obtained in accordance with the invention generally plays a relatively minor role.

Particularly advantageously, the proportion of the different pore diameters in the total pore volume in annular unsupported catalysts obtained in accordance With the invention has the following distribution:

Pores having a diameter in the range of <0.03 µm: ☐ 0 and ☐ 5% by volume, preferably ☐ 3% by volume, Pores having a diameter in the range from ☐ 0.03 to ☐ 0.1 µm: ☐ 3 or ☐ 5 and ☐ 20 or ☐ 15% by volume;

Pores having a diameter in the range from >0.1 to <1 µm: ☐ 75 or ☐ 80 and ☐ 95 or ☐ 90% by volume;

Pores having a diameter in the range from ☐ 1 µm to ☐ 10 µm: ☐ 0 and ☐ 5% by volume, preferably ☐ 3% by volume.

Both the at least one catalyst bed I and the at least one catalyst bed II may be a fluidized bed, moving bed or a fixed bed. The different catalyst beds may be disposed either in one reactor or in different reactors connected in series. The different bed types may of course also be employed in combination. In the simplest case, both the at least one catalyst bed I and the at least one catalyst bed II are each a fixed bed which are each disposed in a single reactor, preferably in a tube bundle reactor.

Advantageously in accordance with the invention, the overall catalyst charge used may be structured, for example, as follows (in the flow direction of the reaction gas mixture):
a) catalyst bed I/catalyst bed II/catalyst bed I;

or b) catalyst bed I/catalyst bed II/catalyst bed I/catalyst bed II/catalyst bed I;

or c) catalyst bed I/catalyst bed II/catalyst bed I/catalyst bed II/catalyst bed I/catalyst bed II/catalyst bed I, etc. Catalyst beds of the same type may quite possibly be different from each other.

When the catalyst beds are disposed in different reactors, the reaction gas mixture may optionally be supplemented by inert gas and/or oxygen at the transition from one to the other reactor.

Especially when the catalyst beds are disposed in a single reactor, the reaction gas mixture is, however, generally retained at the transition from one catalyst bed to the other catalyst bed. In other words, the reaction gas mixture leaving the preceding catalyst bed is normally equivalent to the reaction gas mixture entering the following catalyst bed.

However, the process according to the invention may also be configured in such a way that the overall catalyst charge has, for example, one of the following structures:
a) catalyst bed I/catalyst bed II;

or b) catalyst bed I/catalyst bed II/catalyst bed I/catalyst bed II;

or c) catalyst bed I/catalyst bed II/catalyst bed I/catalyst bed II/catalyst bed I/catalyst bed II etc. Catalyst beds of the same type may quite possibly be different from each other.

In other words, the end point of the overall charge may also be formed by a catalyst bed II.

Especially in the case of the charge structure a), the process according to the invention is performed when target product present in the reaction gas mixture leaving the catalyst bed II forming the final bed is removed therefrom and remaining residual product gas mixture is recycled as cycle gas and fed back to the reaction stage as a constituent of starting reaction gas mixture, as recommended, for example, in DE-A 10316465 and in EP-A 1193240.

The individual catalyst beds in the process according to the invention may be kept at substantially uniform or at different temperature (in this document, temperature of a catalyst bed refers to the temperature of the catalyst bed when the process is performed, but in the theoretical absence of a chemical reaction (i.e. without the influence of the heat of reaction)).

When the catalyst beds are disposed in different reactors, the setting of different bed temperatures is trivial. However, even when they are disposed in one and the same reactor, a different catalyst bed temperature is possible in a simple manner by employing a multizone reactor as described for the case of tube bundle reactors by DE-A 19910506, DE-A 10313213, DE-A 10313208 and EP-A 1106598.

A uniform catalyst bed temperature can be realized, for example, in a simple manner in a one-zone multiple catalyst tube fixed bed reactor, as described by DE-A 4431957, EP-A 700714 and EP-A 700893.

It is essential to the invention that a catalyst bed I or II may consist only of catalysts I or II respectively. The catalysts I and II in the particular catalyst bed may of course also be diluted with inert shaped diluent bodies. Useful materials for such inert shaped diluent bodies include all of those of which the support bodies for the coated catalysts may also consist. The geometry of the particular shaped diluent bodies preferably corresponds to that of the catalysts to be diluted. However, they may also be different from their geometry. In addition, the fraction of the inert shaped diluent bodies may decrease continuously, abruptly or stepwise in the flow direction of the reaction gas mixture within an individual catalyst bed. Between the individual catalyst beds may be disposed, if required in the process according to the invention, pure inert shaped diluent bodies.

The temperature of type I catalyst beds is, advantageously in accordance with the invention, from 200 to 550° C., frequently from 230 to 480° C. or from 300 to 440° C.

The temperature of type II catalyst beds is, advantageously in accordance with the invention, from 250 to 400° C., advantageously from 300 to 380° C. However, it may also be up to 550° C., corresponding to the temperature of type I catalyst beds.

Useful sources for the molecular oxygen required in the process according to the invention may be, for example, air, oxygen-enriched or oxygen-depleted air or pure oxygen.

Otherwise, the reaction gas mixture may comprise, in addition to the saturated hydrocarbon precursor compound and molecular oxygen and also any steam, inert diluent gases (this refers quite generally to those gases of which, in the process according to the invention (based on single pass) more than 95 mol %, preferably more than 98 mol %, remain chemically unchanged), for example $N_2$ and $CO_2$. Frequently, the starting reaction gas mixture also comprises CO (for example in the case of the cycle gas method).

In other words, the starting reaction gas mixture with which the entire catalyst charge is to be charged at pressures of generally from 1 to 10 bar, or from 2 to 5 bar (reduced pressure may in principle also be employed) may have, for example, the following contents:
from 1 to 15 or 20, preferably from 1 to 10 or 7, % by volume of precursor compound (for example propane),
from 0 or 5 to 25 or 50% by volume of steam and
from 10 to 80% by volume of air.

However, it may also have the following contents:
from 2 to 10% by volume of precursor compound (for example propane),
from 5 to 20% by volume of steam,
from 60 to 85% by volume of nitrogen, and
from 5 to 15% by volume of oxygen.

According to the invention, the starting reaction gas mixture used may otherwise be a starting reaction gas mixture as described in the documents EP-A 608838, WO 0029106, JP-A 10-36311, DE-A 10316465, EP-A 1192987, EP-A 1192982, EP-A 1193240 and DE-A 10338529.

In other words, the starting reaction gas mixture may also contain:
from 0.5 to 2% by volume of propane,
from 1 to 6% by volume of water and
a remainder of substantially air.

Multimetal oxide active compositions deactivated in the process according to the invention may be reactivated as described in DE-A 10338529.

When the saturated hydrocarbon used in the process according to the invention is crude propane, its composition is preferably as described in DE-A 10246119, or DE-A 10118814, or WO 02/83615.

The start-up of a fresh catalyst charge may be carried out as described in DE-A 10122027.

Based on the propane and/or isobutane present in the starting reaction gas mixture, the conversion of propane and/or isobutane in the process according to the invention, based on single pass of the reaction gas mixture through the overall catalyst charge (the sum of all individual catalyst beds arranged in succession), will generally be from 10 or 20 to 90 or 70 mol %, frequently from 30 to 60 mol % and in many cases from 40 to 60 mol % or from 45 to 55 mol %.

The selectivity of target product formation will typically be from 40 to 98 or 95 or 90 mol %, in many cases from 50 to 80 mol %, often from 60 to 80 mol %.

The target product removal and any cycle gas control may be as described in DE-A 10316465.

The hourly space velocity on the entire catalyst charge (not including pure inert zones) of propane and/or isobutane may be from 10 to 1000 l (STP)/l (catalyst charge)/h or from 20 to 800 l (STP)/l/h, or from 50 to 600 l (STP)/l/h, or from 100 to 500 l (STP)/l/h, or from 150 to 300 l (STP)/l/h.

The hourly space velocity on the overall catalyst charge (not including pure inert zones) of starting reaction gas mixture may be from 10 to 10 000 l (STP)/l/h, or from 300 to 6000 l (STP)/l/h or from 600 to 3000 l (STP)/l/h. The average residence time in the catalyst charge may be from 0.01 to 10 s, or from 0.1 to 10 s, or from 2 to 6 s.

One catalyst bed I in the process according to the invention may of course contain more than one catalyst I. Equally, one catalyst bed II may contain more than one catalyst II. The catalysts I and II used may also vary along the catalyst charge.

In general, it is advantageous in accordance with the invention when the catalysts used in the region of low conversions of the at least one saturated hydrocarbon precursor compound are catalysts I whose dependence between conversion and selectivity of target product formation is such that the selectivity of target product formation at low conversions (e.g. ≦15 mol %) is particularly high (e.g. ≧60 mol %) and falls sharply with increasing conversion, while the catalysts used in the region of higher conversions of the at least one saturated hydrocarbon compound are catalysts I whose dependence between conversion and selectivity of target product formation is such that the selectivity of target product formation rises more slowly with the conversion up to conversions of above 20 mol %, but also persists with higher conversion and falls only slowly.

Finally, it should be emphasized once again that multimetal oxide active compositions II have an X-ray diffractogram which is different to that of the multimetal oxide active compositions. In general, it contains neither the reflection i nor the reflection k.

EXAMPLES AND COMPARATIVE EXAMPLES

A) Preparation of a Spherical Coated Catalyst I
Stoichiometry of the Active Composition:
$Mo_{1.0}V_{0.29}Te_{0.14}Nb_{0.13}O_x$ 87.61 g of ammonium metavanadate (78.55% by weight of $V_2O_5$, from G.f.E., Nuremberg, Germany) were dissolved at 80° C. in 3040 ml of water in a glass three-necked flask equipped with stirrer, thermometer, reflux condenser and heater. This gave a clear yellowish solution. This solution was cooled to 60° C. and then, successively in the sequence specified, while maintaining the 60° C., first 117.03 g of telluric acid (99% by weight of $H_6TeO_6$, from Aldrich) and then 400 g of ammonium heptamolybdate tetrahydrate (82.52% by weight of $MoO_3$, from Starck, Goslar, Germany) were stirred in. The resulting deep red solution was cooled to 30° C. and a solution A was obtained in this way.

In a beaker, 112.67 g of ammonium niobium oxalate (20.8% by weight of Nb, from Starck, Goslar, Germany) in 500 ml of water were added separately at 60° C. to give a solution B. Solution B was likewise cooled to 30° C. and combined at this temperature with solution A by stirring solution B into solution A. The stirring-in was effected continuously within a period of 5 minutes. This gave an orange-colored aqueous suspension.

This suspension was subsequently spray-dried ($T_{reservoir}$=30° C., $T^{in}$=320° C., $T^{out}$=110° C., drying time: approx. 1.5 h, spray tower from Niro, Germany, of the Atomizer type). The sprayed material was likewise orange.

1% by weight of finely divided graphite (sieve analysis: min. 50% by weight ≦24 μm, max. 10% by weight >24 μm and ≦48 μm, max. 5% by weight >48 μm, BET surface area: from 6 to 13 m²/g was mixed into the sprayed material.

The resulting mixture was compacted (compressed) to hollow cylinders (rings) of geometry 16 mm×2.5 mm×8 mm (external diameter×height×internal diameter) in such a way that the resulting side crushing strength of the rings was approx. 10 N.

200 g of these rings were calcined in two portions each of 100 g successively in a rotary sphere furnace according to FIG. 1 of DE-A 10122027. To this end, the rotary sphere furnace contents were heated from 25° C. to 275° C. within 27.5 min with a linear heating ramp under an air stream of 50 l (STP)/h, and kept at this temperature for 1 h while maintaining the air stream. Subsequently, the furnace was heated from 275° C. to 600° C. with a linear heating ramp within 32.5 min, in the course of which the air stream was replaced by a nitrogen stream of 50 l (STP)/h. The 600° C. and the nitrogen stream were maintained for 2 h and the entire furnace was subsequently left to cool to 25° C. while maintaining the nitrogen stream. This resulted in black rings of the composition $Mo_{1.0}V_{0.33}Te_{0.19}Nb_{0.11}O_x$ (stoichiometry: $Mo_{1.0}V_{0.33}Te_{0.22}Nb_{0.11}O_x$).

In a Retsch mill, the rings were ground dry to a particle size of ≦100 μm. 100 g of the ground material were stirred under reflux at 70° C. in 1000 ml of a 10% by weight aqueous $HNO_3$ solution over 7 h, and the solid was filtered out of the resulting slurry and washed with water to free it of nitrate. The filtercake was dried in a muffle furnace at 110° C. under air overnight. The resulting active composition had the composition $Mo_{1.0}V_{0.29}Te_{0.14}Nb_{0.13}O_x$. Its X-ray diffractogram (cf. FIG. 1) revealed pure i phase having R=0.74. It contained no reflection having the peak location 2Θ=50.0±0.3°.

Figure 2:
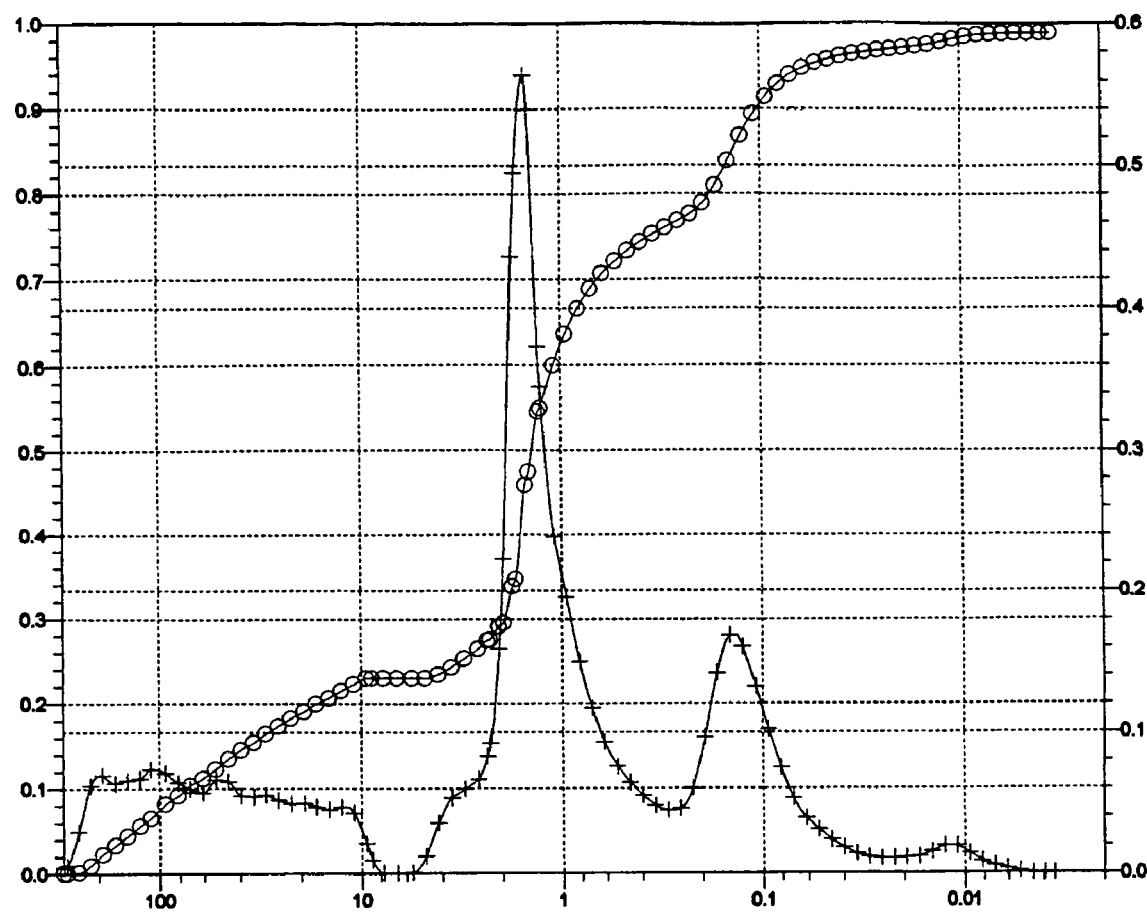
FIG. 2 shows a mercury porosimmetry curve of pore diameter of the composition of FIG. 1.
Figure 3:
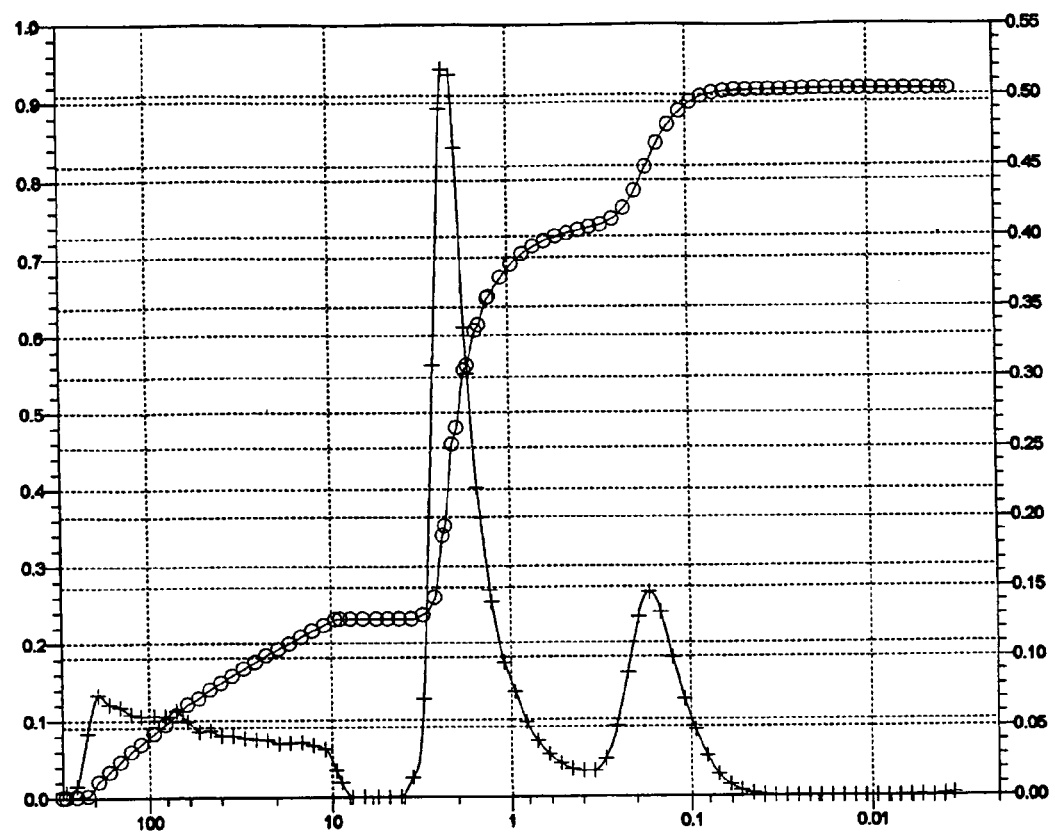
FIG. 3 shows a mercury porosimmetry curve for the composition of FIG. 1 before washing with nitric acid.

FIG. 2 shows the result of the accompanying mercury porosymmetry investigation. The abscissa shows the pore diameter in μm (logarithmic plot). The right ordinate (o curve) shows the integral over the contributions of the individual pore diameter to the total pore volume in ml/g. The left ordinate (+curve) shows the logarithm of the contribution of the individual pore diameter to the total pore volume in ml/g. FIG. 3 shows the corresponding investigation result for the ground rings before their washing with nitric acid.

75 g of the resulting active composition powder were applied to 300 g of spherical support bodies having a diameter of 2.2–3.2 mm (support material=steatite of the C220 type from CeramTec, Germany, total pore volume of the support ≦1% by volume based on the total support volume; $R_z$=45 μm). To this end, the support bodies were initially charged in a coating drum having a capacity of 2 l (inclination angle of the central drum axis relative to the horizontal=30°). The drum was rotated at 25 revolutions per minute. An atomizer nozzle operated with 300 l (STP)/h of compressed air was used to spray approx. 30 ml of a mixture of glycerol and water (glycerol:water weight ratio=1:3) onto the support bodies over 60 min. The nozzle was installed in such a way that the spray cone wetted the support bodies conveyed within the drum to the uppermost point of the inclined drum by means of carrier plates, in the upper half of the roll-off section. The finely divided active composition powder was introduced into the drum via a powder screw, although the point of powder addition within the roll-off section was below the spray cone. The periodic repetition of wetting and powder-replenishment resulted in the initially coated support body itself becoming the support body in the subsequent period.

On completion of coating, the coated support bodies were dried in a muffle furnace at 150° C. over 16 hours. A coated catalyst S20 to be used in accordance with the invention and having an active composition fraction of 20% by weight was obtained (catalyst I).

B) Preparation of an Annular Unsupported Catalyst II Having the Following Stoichiometry of the Active Multimetal Oxide II

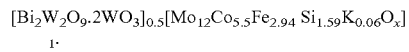

1. Preparation of a Starting Composition 1

209.3 kg of tungstic acid (72.94% by weight of W) were stirred in portions into 775 kg of an aqueous bismuth nitrate solution in nitric acid (11.2% by weight of Bi; free nitric acid from 3 to 5% by weight; mass density: from 1.22 to 1.27 g/ml) at 25° C. The resulting aqueous mixture was subsequently stirred at 25° C. for a further 2 h and subsequently spray-dried.

The spray-drying was effected in a rotating disk spray tower in countercurrent at a gas inlet temperature of 300±10° C. and a gas outlet temperature of 100±10° C. The resulting spray powder (particle size a substantially uniform 30 μm) which had an ignition loss of 12% by weight (ignite at 600° C. under air for 3 h) was subsequently converted to a paste in a kneader using 16.8% by weight (based on the powder) of water and extruded by means of an extruder (rotational moment: ☐ 50 Nm) to extrudates of diameter 6 mm. These were cut into sections of 6 cm, dried under air on a 3-zone belt dryer at a residence time of 120 min at temperatures of 90–95° C. (zone 1) and 125° C. (zone 2) and 125° C. (zone 3), and then thermally treated at a temperature in the range from 780 to 810° C. (calcined; in a rotary tube oven flowed through by air (capacity 1.54 m³, 200 m³ (STP) of air/h)). When precisely adjusting the calcination temperature, it is essential that it has to be directed to the desired phase composition of the calcination product. The desired phases are $WO_3$ (monoclinic) and $Bi_2W_2O_9$; the presence of ≻$Bi_2WO_6$ (Russellite) is undesired. Therefore, should the compound ≻$Bi_2WO_6$ still be detectable by a reflection in the X-ray powder diffractogram after the calcination at a reflection angle of 2Θ=28.4° (Cukα radiation), the preparation has to be repeated and the calcination temperature increased within the temperature range specified or the residence time increased at constant calcination temperature, until the disappearance of the reflection is achieved. The preformed calcined mixed oxide obtained in this way was ground so that the $X_{50}$ value (cf. Ullmann's Encyclopedia of Industrial Chemistry, 6$^{th}$ Edition (1998) Electronic Release, Chapter 3.1.4 or DIN 66141) of the resulting particle size was 5 mm. The ground material was then mixed with 1% by weight (based on the ground material) of finely divided $SiO_2$ from Degussa of the Sipernat® type (bulk density 150 g/l; $X_{50}$ value of the $SiO_2$ particles was 10 μm, the BET surface area was 100 m²/g).

2. Preparation of a Starting Composition 2

A solution A was prepared by dissolving 213 kg of ammonium heptamolybdate tetrahydrate (81.5% by weight of $MoO_3$) at 60° C. with stirring in 600 l of water and the resulting solution was admixed while maintaining the 60° C. and stirring with 0.97 kg of an aqueous potassium hydroxide solution (46.8% by weight of KOH) at 20° C.

A solution B was prepared by introducing 116.25 kg of an aqueous iron(III) nitrate solution (14.2% by weight of Fe) at 60° C. into 262.9 kg of an aqueous cobalt(II) nitrate solution (12.4% by weight of Co). Subsequently, while maintaining the 60° C., solution B was continuously pumped into the initially charged solution A over a period of 30 minutes. Subsequently, the mixture was stirred at 60° C. for 15 minutes. 19.16 kg of a Ludox silica gel from Dupont (46.80% by weight of $SiO_2$, density: from 1.36 to 1.42 g/ml, pH from 8.5 to 9.5, max. alkali content 0.5% by weight) were then added to the resulting aqueous mixture, and the mixture was stirred afterward at 60° C. for a further 15 minutes.

Subsequently, the mixture was spray-dried in countercurrent in a rotating disc spray tower (gas inlet temperature: 400±10° C., gas outlet temperature: 140±5° C.). The resulting spray powder had an ignition loss of approx. 30% by weight (ignite under air at 600° C. for 3 h) and a substantially uniform particle size of 30 μm.

3. Preparation of the Multimetal Oxide Active Composition II

The starting composition 1 was mixed homogeneously with the starting composition 2 in the amounts required for a multimetal oxide active composition of the stoichiometry

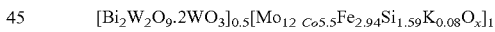

in a mixer having bladed heads. Based on the aforementioned overall composition, an additional 1% by weight of finely divided graphite from Timcal AG (San Antonio, US) of the TIMREX P44 type (sieve analysis: min. 50% by weight <24 μm, max. 10% by weight ☐ 24 μm and ☐ 48 μm, max. 5% by weight >48 μm, BET surface area: from 6 to 13 m²/g) were mixed in homogeneously. The resulting mixture was then conveyed in a compactor (from Hosokawa Bepex GmbH, D-74211 Leingarten) of the K200/100 compactor type having concave, fluted smooth rolls (gap width: 2.8 mm, sieve width: 1.0 mm, lower particle size sieve width: 400 μm, target compressive force: 60 kN, screw-rotation rate: from 65 to 70 revolutions per minute). The resulting compactate had a hardness of 10 N and a substantially uniform particle size of from 400 μm to 1 mm.

The compactate was subsequently mixed with, based on its weight, a further 2% by weight of the same graphite and subsequently compressed in a Kilian rotary tableting press of the Rx73 type from Kilian, D-50735 Cologne, under a nitrogen atmosphere to give annular shaped unsupported catalyst precursor bodies of geometry (external diameter ☐ length □ internal diameter) 5 mm □ 3 mm □ 2 mm and having a side crushing strength of 19 N.

In this document, side crushing strength refers to the crushing strength when the annular shaped unsupported catalyst precursor body is compressed at right angles to the cylinder surface (i.e. parallel to the surface of the ring orifice).

All side crushing strengths in this document relate to a determination by means of a material testing machine from Zwick GmbH & Co. (D-89079 Ulm) of the Z 2.5/TS1 S type. This material testing machine is designed for quasistatic stress having an uninterrupted, stationary, dynamic or varying profile. It is suitable for tensile, compressive and bending tests. The installed force transducer of the KAF-TC type from A.S.T. (D-01307 Dresden) having the manufacturer number 03–2038 was calibrated in accordance with DIN EN ISO 7500-1 and could be used for the 1–500 N measurement range (relative measurement uncertainty: ±0.2%).

The measurements were carried out with the following parameters:
Initial force: 0.5 N.
Rate of initial force: 10 mm/min.
Testing rate: 1.6 mm/min.

The upper die was initially lowered slowly down to just above the cylinder surface of the annular shaped unsupported catalyst precursor body. The upper die was then stopped, in order subsequently to be lowered at the distinctly slower testing rate with the minimum initial force required for further lowering.

The initial force at which the shaped unsupported catalyst precursor body exhibits crack formation is the side crushing strength (SCS).

For the final thermal treatment, in each case 1000 g of the shaped unsupported catalyst precursor bodies were heated in a muffle furnace flowed through by air (capacity 60 l, 1 l/h of air per gram of shaped unsupported catalyst precursor body) initially from room temperature (25° C.) to 190° C. at a heating rate of 180° C./h. This temperature was maintained for 1 h and then increased to 210° C. at a heating rate of 60° C./h. The temperature of 210° C. was in turn maintained over 1 h before it was increased to 230° C. at a heating rate of 60° C./h. This temperature was likewise maintained for 1 h before it was increased to 265° C., again at a heating rate of 60° C./h. The temperature of 265° C. was subsequently likewise maintained over 1 h. Afterward, the furnace was initially cooled to room temperature and the decomposition phase thus substantially completed. The furnace was then heated to 465° C. at a heating rate of 180° C./h and this calcination temperature maintained over 4 h.

Annular unsupported catalysts II were obtained from the annular shaped unsupported catalyst precursor bodies.

The specific surface area S, the total pore volume V, the pore diameter $d^{max}$ which makes the greatest contribution to the total pore volume, and the percentages of those pore diameters in the total pore volume whose diameter is >0.1 and ≦1 μm, for the resulting annular unsupported catalysts were as follows:
S=7.6 cm²/g.
V=0.27 cm³/g.
$d^{max}$ [μm]=0.6.
$V^{0.1}_1$-%=79.

In addition, the ratio R of apparent mass density to true mass density p (as defined in EP-A 1340538) was 0.66.

C) Preparation of a Comparative Catalyst Replacing a Catalyst II and Having the Following Stoichiometry of the Active Multimetal Oxide $$Mo_{12}V_3W_{1.2}Cu_{2.4}O_x.$$

The preparation was effected as in preparation example 5 of DE-A 10046928. The comparative catalyst was an annular coated catalyst of geometry 7 mm×3 mm×4 mm. The coated catalysts had an active composition fraction of 20% by weight.

D) Heterogeneously Catalyzed Gas Phase Partial Oxidation of Propane to Acrylic Acid a) Comparative Example 1

35.0 g of the coated catalyst S20 from A) were installed into a single-tube reactor (tube length: 140 cm, internal diameter: 8.5 mm, external diameter: 60 mm, V2A steel, catalyst bed length: 51.5 cm, additionally to heat the starting reaction gas mixture, a 30 cm-long preliminary bed of steatite spheres from CeramTec (C220, diameter 2.2–3.2 mm), and the reaction tube was also finally charged with the same steatite spheres as the catalyst charge) which was heated by an electrical heating mat. At a mat temperature of 350° C., the coated catalyst was installed into the tubular reactor under air.

Afterward, the reaction tube was charged while maintaining the mat temperature of 350° C. for 24 h with a starting reaction gas mixture (charge gas mixture) which had the following composition:

propane:air:$H_2O$=1:15:14 (ratio of the molar amounts).

The residence time (based on the catalyst bed volume) selected was 2.4 s, and the reaction tube inlet pressure was 2 bar absolute. The GHSV was 1500 h$^{-1}$ (based on charge gas mixture).

Subsequently, the heating mat temperature was increased to 380° C. The propane conversion (based on single pass) was 40 mol % and the selectivity of acrylic acid formation was 68 mol %.

b) Example 1

Everything was carried out as in comparative example 1. However, the 35.0 g of coated catalyst S20 from A) were replaced by the following catalyst charge structure (looking in the flow direction of the reaction gas mixture):

21 g of cat. I from A), 7 g of cat. II from B), 7 g of cat. I from A).

The GHSV (of charge gas mixture) on the total amount of cat. I from A) was likewise 1500 h$^{-1}$.

At a heating mat temperature of 380° C., the propane conversion was 39 mol % and the selectivity of acrylic acid formation was 72 mol %.

c) Example 2

Everything was carried out as in comparative example 1. However, the 35.0 g of coated catalyst S20 from A) were replaced by the following catalyst charge structure (looking in the flow direction of the reaction gas mixture):

7 g of cat. I from A), 7 g of cat. II from B), 7 g of cat. I from A), 7 g of cat. II from B), 7 g of cat. I from A).

The GHSV (of charge gas mixture) on the total amount of cat. I from A) was likewise 1500 h$^{-1}$.

At a heating mat temperature of 380° C., the propane conversion was 39 mol % and the selectivity of acrylic acid formation was 74 mol %.

d) Comparative Example 2

Everything was carried out as in example 1, except that 7 g of cat. II from B) were replaced by 7 g of comparative catalyst from C). At a heating mat temperature of 380° C., the propane conversion was 38 mol % and the selectivity of acrylic acid formation was 34 mol %.

U.S. Provisional Patent Application No. 60/504,957, filed on Sep. 23, 2003, is incorporated into the present application by way of reference.

With regard to the abovementioned teachings, numerous alterations and deviations from the present invention are possible. It may therefore be assumed that the invention, within the scope of the appended claims, may be performed differently than specifically described herein.

We claim:

1. A process for preparing (meth)acrylic acid by heterogeneously catalyzed gas phase partial oxidation of at least one saturated hydrocarbon precursor compound at elevated temperature, by conducting a starting reaction gas mixture comprising the at least one saturated hydrocarbon precursor compound, molecular oxygen and at least one inert gas through at least one catalyst bed I whose catalysts I are such that their active composition is at least one multimetal oxide I which contains the elements Mo and V, at least one of the elements Te and Sb, and at least one of the elements from the group consisting of Nb, Ta, W, Ce and Ti, and whose X-ray diffractogram is an X-ray diffractogram I which has reflections h, i and k whose peak locations are at the reflection angles (2Θ) of 22.2±0.5° (h), 27.3±0.5° (i) and 28.2±0.5° (k), the reflection h being the most intense within the X-ray diffractogram I and also having a half-height width of at most 0.5°, and the half-height width of the reflection i and of the reflection k each being ≦1°, wherein the gas phase partial oxidation of the reaction gas mixture over the catalysts I in the at least one catalyst bed I is interrupted at least once by continuing the gas phase partial oxidation in at least one catalyst bed II whose catalysts II are such that their active composition is at least one multimetal oxide II whose X-ray diffractogram is different to the X-ray diffractogram I and has a stoichiometry of the general formula A, $$Mo_{12}Bi_aFe_bX^1_cX^2_dX^3_eX^4_fO_n \quad (A)$$

where

X$^1$=nickel and/or cobalt,

X$^2$=thallium, an alkali metal and/or an alkaline earth metal,

X$^3$=zinc, phosphorus, arsenic, boron, antimony, tin, cerium, lead and/or tungsten, X$^4$=silicon, aluminum, titanium and/or zirconium, a=from 0.2 to 5, b=from 0.01 to 5, c=from 0 to 10, d=from 0 to 2, e=from 0 to 8, f=from 0 to 10 and n=a number which is determined by the valency and frequency of the elements in A other than oxygen, or a stoichiometry of the general formula B $$[Y^1_{a'}Y^2_{b'}O_{x'}]_p[Y^3_{c'}Y^4_{d'}Y^5_{e'}Y^6_{f'}Y^7_{g'}Y^2_{h'}O_{y'}]_q \quad (B)$$

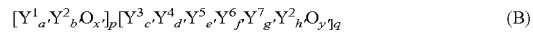

where

Y$^1$=only bismuth or bismuth and at least one of the elements tellurium, antimony, tin and copper, Y$^2$=molybdenum or molybdenum and tungsten, Y$^3$=an alkali metal, thallium and/or samarium, Y$^4$=an alkaline earth metal, nickel, cobalt, copper, manganese, zinc, tin, cadmium and/or mercury, Y$^5$=iron or iron and at least one of the elements vanadium, chromium and cerium, Y$^6$=phosphorus, arsenic, boron and/or antimony, Y$^7$=a rare earth metal, titanium, zirconium, niobium, tantalum, rhenium, ruthenium, rhodium, silver, gold, aluminum, gallium, indium, silicon, germanium, lead, thorium and/or uranium, a'=from 0.01 to 8, b'=from 0.1 to 30, c'=from 0 to 4, d'=from 0 to 20, e'=from >0 to 20, f'=from 0 to 6, g'=from 0 to 15, h'=from 8 to 16, x', y'=numbers which are determined by the valency and frequency of the elements in B other than oxygen and p, q=numbers whose p/q ratio is from 0.1 to 10.

2. A process as claimed in claim 1, wherein the at least one catalyst bed I and the at least one catalyst bed II are each one fixed bed.

3. The process of claim 1, wherein the multimetal oxide I has an X-ray diffractogram wherein the intensity P$^i$ of the reflection i and the intensity P$_k$ of the reflection k have a ratio R of 0.55≦R≦0.85 where R is defined by R=P$_i$/(P$_i$+P$_k$).

4. The process according to claim 3, wherein 0.65≦R≦0.85.

5. The process according to claim 3, wherein R is from 0.69 to 0.75.

6. The process according to claim 1, wherein the multimetal oxide I has further reflection angles (2θ) of 9.0±0.4° (l) 6.7±0.4° (o); and 7.9±0.4° (p).

7. The process according to claim 1, wherein the multimetal oxide I has a formula:

$$MO_1V_aM^1_bM^2_cM^3_dO_n$$

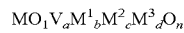

where M$^1$ is at least one of Te and Sb;

M$^2$ is at least one of Nb, Ti, W, Ta and Ce;

M$^3$ is at least one selected from the group consisting of Pb, Ni, Co, Bi, Pd, Ca, Mg, Fe, Mn, Ag, Pt, Cu, Au, Ga, Zn, Sn, In, Re, Ir, Sm, Sc, Y, Pr, Nd, and Tb;

a is from 0.01 to 1;

b is from 0.01 to 1;

c is from 0.01 to 1;

d is from 0 to 0.5; and n is determined by the valency and frequency of the elements other than oxygen.

8. The process according to claim 7 wherein:

a is from 0.05 to 0.6;

b is from 0.01 to 1;

c is from 0.01 to 1; and d is from 0.0005 to 0.5.

9. The process according to claim 7, wherein:

a is from 0.1 to 0.6;

b is from 0.1 to 0.5;

c is from 0.05 to 0.1; and
d is from 0.01 to 0.5.

10. The process according to claim 7, wherein $M^1$ is Te; and $M^2$ is Nb.

11. The process according to claim 1, wherein the X-ray diffractogram of the multimetal oxide I has no 2θ reflection at 50±0.3°.

12. The process according to claim 1, wherein the gas mixture comprises from 1 to 20% by volume of at least one saturated hydrocarbon precursor, from 0 to 50% by volume of steam, and from 10 to 80% by volume of air.

13. The process according to claim 1, wherein the gas mixture comprises from 1 to 10% by volume of at least one saturated hydrocarbon precursor, from 5 to 25% by volume of steam, and from 10 to 80% by volume of air.

14. The process according to claim 1, wherein the gas mixture comprises from a 2 to 10% by volume of the saturated hydrocarbon precursor, from 5 to 20% by volume of steam, from 60 to 85% by volume of nitrogen, and from 5 to 15% by volume of oxygen.

15. The process according to claim 14, wherein the saturated hydrocarbon precursor compound comprises propane.

16. The process according to claim 1, wherein the multimetal oxide I is present in the form of an annular unsupported catalyst wherein the pores having a diameter less than 0.03 μm are from 0 to 5% by volume of the total pore volume.

17. The process according to claim 1, wherein the multimetal oxide I is present in the form of an unsupported annular catalyst wherein the pores having a diameter in the range of from 0.3 to 0.1 μm are from 20 to 15% by volume of the total pore volume.

18. The process according to claim 1, wherein the multimetal oxide I is present in the form of an unsupported annular catalyst wherein pores having a diameter in the range of from >0.1 to <1 μm are greater than 75% of the total volume of the pores.

* * * * *